US005635599A

United States Patent [19]

Pastan et al.

[11] Patent Number: 5,635,599

[45] Date of Patent: Jun. 3, 1997

[54] FUSION PROTEINS COMPRISING CIRCULARLY PERMUTED LIGANDS

[75] Inventors: Ira H. Pastan; Robert J. Kreitman, both of Potomac; Raj K. Puri, North Potomac, all of Md.

[73] Assignee: The United States of America as represented by the Department of Health and Human Services, Washington, D.C.

[21] Appl. No.: 225,224

[22] Filed: Apr. 8, 1994

[51] Int. Cl.[6] ........................ C07K 19/00; C07K 14/535; C07K 14/55; C07K 14/54

[52] U.S. Cl. ........................ 530/351; 530/350; 435/69.1; 435/69.5; 435/69.52; 435/69.7; 435/172.3

[58] Field of Search ........................ 530/351, 350; 514/12, 2; 435/69.1, 69.5, 69.52, 69.7, 172.3

[56] References Cited

FOREIGN PATENT DOCUMENTS

| | | |
|---|---|---|
| 370205 | 5/1990 | European Pat. Off. . |
| 367166 | 5/1990 | European Pat. Off. . |

OTHER PUBLICATIONS

*The Journal of Biological Chemistry*, vol. 268, No. 19, 5 Jul. 1993 pp. 14065–14070, Waldemar Debinski et al. see p. 14068, first paragraph of the Discussion.

*Science*, vol. 245, 29 Sep. 1989 pp. 1493–1496, Cynthia E. Dunbar et al., 'Carboxyl–terminal–modified interleukin–3 is retained intracellularly and stimulates autocrine growth' see the whole document.

*Cancer Research*, vol. 55, No. 15, 1 Aug. 1995 pp. 3357–3363, Robert J. Kreitman et al., 'Increased antitumor activity of a circularly permuted interleukin 4–toxin in mice with interleukin 4 receptor–bearing human carcinoma'.

Pastan et al. 1992. Ann. Rev. Biochem. 61:331–54.

Ogata et al. 1989. PNAS USA 86:4215–9.

Puri et al. 1991. J. Cancer Res. 51:3011–7.

Pastan et al. 1991. Science 254:1173–7.

Kreitman et al. Jul. 1994. PNAS USA 91: 6889–93.

Buchwalder, et al., A fully active variant of dihydrofolate reductase with a circularly permuted sequence. *Biochemistry,* 31: 1621–1630 (1992).

Cunningham, et al., Favin versus concanavalin A: circularly permuted amino acid sequences. *Proc. Natl. Acad. Sci. USA,* 76: 3218–3222 (1979).

Goldenberg, et al. Circular and circularly permuted forms of bovine pancreatic trypsin inhibitor. *J. Mol. Biol.,* 165: 407–413 (1983).

Goldenberg, Circularly permuted proteins. *Protein Eng.,* 7: 493–495 (1989).

Hoppe, et al., Insulin analogues with permuted A chain N–terminus. *Z. Physiol. Chem.,* 356: 981–986 (1975). (Abstract only).

Horlick, et al., Permuteins of interleukin 1β—a simplified approach for the construction of permutated proteins having new termini. *Protein Eng.,* 5: 427–431 (1992).

Luger, et al., Correct folding of circularly permuted variants of a βα barrel enzyme in vivo. *Science,* 243: 206–210 (1989).

Min, et al., Non–glycosylated recombinant pro–concanavalin A is active without polypeptide cleavage. *E.M.B.O. J.,* 11: 1303–1307 (1992).

Pan, et al. Circularly permuted DNA, RNA and proteins—a review. *Gene,* 125:11–114 (1993).

*Primary Examiner*—Stephen G. Walsh

*Assistant Examiner*—Elizabeth C. Kemmerer

*Attorney, Agent, or Firm*—Townsend and Townsend and Crew

[57] ABSTRACT

The present invention provides for circularly permuted ligands which possess specificity and binding affinity comparable to or greater than the specificity and binding affinity of the original (unpermuted) ligand. The invention further provides for novel fusion proteins comprising a circularly permuted ligand fused to one or more proteins of interest.

17 Claims, 4 Drawing Sheets

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
( A ) LENGTH: 614 amino acids
( B ) TYPE: amino acid
( C ) STRANDEDNESS: unknown
( D ) TOPOLOGY: unknown ( i i ) MOLECULE TYPE: protein -continued ( i x ) FEATURE:

( A ) NAME/KEY: Protein ( B ) LOCATION: 1..614

( D ) OTHER INFORMATION: /label= native-PE ( x i ) SEQUENCE DESCRIPTION: SEQ ID NO:1:

| | | | | | | | | | | | | | | | |
|---|---|---|---|---|---|---|---|---|---|---|---|---|---|---|---|
| Met | Ala | Glu | Glu | Ala | Phe | Asp | Leu | Trp | Asn | Glu | Cys | Ala | Lys | Ala | Cys |
| 1 | | | | 5 | | | | | 10 | | | | | 15 | |
| Val | Leu | Asp | Leu | Lys | Asp | Gly | Val | Arg | Ser | Ser | Arg | Met | Ser | Val | Asp |
| | | | 20 | | | | | 25 | | | | | 30 | | |
| Pro | Ala | Ile | Ala | Asp | Thr | Asn | Gly | Gln | Gly | Val | Leu | His | Tyr | Ser | Met |
| | | 35 | | | | | 40 | | | | | 45 | | | |
| Val | Leu | Glu | Gly | Gly | Asn | Asp | Ala | Leu | Lys | Leu | Ala | Ile | Asp | Asn | Ala |
| | 50 | | | | | 55 | | | | | 60 | | | | |
| Leu | Ser | Ile | Thr | Ser | Asp | Gly | Leu | Thr | Ile | Arg | Leu | Glu | Gly | Gly | Val |
| 65 | | | | | 70 | | | | | 75 | | | | | 80 |
| Glu | Pro | Asn | Lys | Pro | Val | Arg | Tyr | Ser | Tyr | Thr | Arg | Gln | Ala | Arg | Gly |
| | | | | 85 | | | | | 90 | | | | | 95 | |
| Ser | Trp | Ser | Leu | Asn | Trp | Leu | Val | Pro | Ile | Gly | His | Glu | Lys | Pro | Ser |
| | | | 100 | | | | | 105 | | | | | 110 | | |
| Asn | Ile | Lys | Val | Phe | Ile | His | Glu | Leu | Asn | Ala | Gly | Asn | Gln | Leu | Ser |
| | | 115 | | | | | 120 | | | | | 125 | | | |
| His | Met | Ser | Pro | Ile | Tyr | Thr | Ile | Glu | Met | Gly | Asp | Glu | Leu | Leu | Ala |
| | 130 | | | | | 135 | | | | | 140 | | | | |
| Lys | Leu | Ala | Arg | Asp | Ala | Thr | Phe | Phe | Val | Arg | Ala | His | Glu | Ser | Asn |
| 145 | | | | | 150 | | | | | 155 | | | | | 160 |
| Glu | Met | Gln | Pro | Thr | Leu | Ala | Ile | Ser | His | Ala | Gly | Val | Ser | Val | Val |
| | | | | 165 | | | | | 170 | | | | | 175 | |
| Met | Ala | Gln | Thr | Gln | Pro | Arg | Arg | Glu | Lys | Arg | Trp | Ser | Glu | Trp | Ala |
| | | | 180 | | | | | 185 | | | | | 190 | | |
| Ser | Gly | Lys | Val | Leu | Cys | Leu | Leu | Asp | Pro | Leu | Asp | Gly | Val | Tyr | Asn |
| | | 195 | | | | | 200 | | | | | 205 | | | |
| Tyr | Leu | Ala | Gln | Gln | Arg | Cys | Asn | Leu | Asp | Asp | Thr | Trp | Glu | Gly | Lys |
| | 210 | | | | | 215 | | | | | 220 | | | | |
| Ile | Tyr | Arg | Val | Leu | Ala | Gly | Asn | Pro | Ala | Lys | His | Asp | Leu | Asp | Ile |
| 225 | | | | | 230 | | | | | 235 | | | | | 240 |
| Lys | Pro | Thr | Val | Ile | Ser | His | Arg | Leu | His | Phe | Pro | Glu | Gly | Gly | Ser |
| | | | | 245 | | | | | 250 | | | | | 255 | |
| Leu | Ala | Ala | Leu | Thr | Ala | His | Gln | Ala | Cys | His | Leu | Pro | Leu | Glu | Thr |
| | | | 260 | | | | | 265 | | | | | 270 | | |
| Phe | Thr | Arg | His | Arg | Gln | Pro | Arg | Gly | Trp | Glu | Gln | Leu | Glu | Gln | Cys |
| | | 275 | | | | | 280 | | | | | 285 | | | |
| Gly | Tyr | Pro | Val | Gln | Arg | Leu | Val | Ala | Leu | Tyr | Leu | Ala | Ala | Arg | Leu |
| | 290 | | | | | 295 | | | | | 300 | | | | |
| Ser | Trp | Asn | Gln | Val | Asp | Gln | Val | Ile | Arg | Asn | Ala | Leu | Ala | Ser | Pro |
| 305 | | | | | 310 | | | | | 315 | | | | | 320 |
| Gly | Ser | Gly | Gly | Asp | Leu | Gly | Glu | Ala | Ile | Arg | Glu | Gln | Pro | Glu | Gln |
| | | | | 325 | | | | | 330 | | | | | 335 | |
| Ala | Arg | Leu | Ala | Leu | Thr | Leu | Ala | Ala | Ala | Glu | Ser | Glu | Arg | Phe | Val |
| | | | 340 | | | | | 345 | | | | | 350 | | |
| Arg | Gln | Gly | Thr | Gly | Asn | Asp | Glu | Ala | Gly | Ala | Ala | Asn | Ala | Asp | Val |
| | | 355 | | | | | 360 | | | | | 365 | | | |
| Val | Ser | Leu | Thr | Cys | Pro | Val | Ala | Ala | Gly | Glu | Cys | Ala | Gly | Pro | Ala |
| | 370 | | | | | 375 | | | | | 380 | | | | |
| Asp | Ser | Gly | Asp | Ala | Leu | Leu | Glu | Arg | Asn | Tyr | Pro | Thr | Gly | Ala | Glu |

-continued 385 390 395 400

Phe Leu Gly Asp Gly Gly Asp Val Ser Phe Ser Thr Arg Gly Thr Gln
405 410 415

Asn Trp Thr Val Glu Arg Leu Leu Gln Ala His Arg Gln Leu Glu Glu
420 425 430

Arg Gly Tyr Val Phe Val Gly Tyr His Gly Thr Phe Leu Glu Ala Ala
435 440 445

Gln Ser Ile Val Phe Gly Gly Val Arg Ala Arg Ser Gln Asp Leu Asp
450 455 460

Ala Ile Trp Arg Gly Phe Tyr Ile Ala Gly Asp Pro Ala Leu Ala Tyr
465 470 475 480

Gly Tyr Ala Gln Asp Gln Glu Pro Asp Ala Arg Gly Arg Ile Arg Asn
485 490 495

Gly Ala Leu Leu Arg Val Tyr Val Pro Arg Ser Ser Leu Pro Gly Phe
500 505 510

Tyr Arg Thr Ser Leu Thr Leu Ala Ala Pro Glu Ala Ala Gly Glu Val
515 520 525

Glu Arg Leu Ile Gly His Pro Leu Pro Leu Arg Leu Asp Ala Ile Thr
530 535 540

Gly Pro Glu Glu Glu Gly Gly Arg Leu Glu Thr Ile Leu Gly Trp Pro
545 550 555 560

Leu Ala Glu Arg Thr Val Val Ile Pro Ser Ala Ile Pro Thr Asp Pro
565 570 575

Arg Asn Val Gly Gly Asp Leu Asp Pro Ser Ser Ile Pro Asp Lys Glu
580 585 590

Gln Ala Ile Ser Ala Leu Pro Asp Tyr Ala Ser Gln Pro Gly Lys Pro
595 600 605

Pro Arg Glu Asp Leu Lys
610

( 2 ) INFORMATION FOR SEQ ID NO:2:

( i ) SEQUENCE CHARACTERISTICS:
( A ) LENGTH: 129 amino acids
( B ) TYPE: amino acid
( C ) STRANDEDNESS: unknown
( D ) TOPOLOGY: unknown ( i i ) MOLECULE TYPE: protein ( i x ) FEATURE:
( A ) NAME/KEY: Protein
( B ) LOCATION: 1..129
( D ) OTHER INFORMATION: /label= IL4

( x i ) SEQUENCE DESCRIPTION: SEQ ID NO:2:

His Lys Cys Asp Ile Thr Leu Gln Glu Ile Ile Lys Thr Leu Asn Ser
1 5 10 15

Leu Thr Glu Gln Lys Thr Leu Cys Thr Glu Leu Thr Val Thr Asp Ile
20 25 30

Phe Ala Ala Ser Lys Asn Thr Thr Glu Lys Glu Thr Phe Cys Arg Ala
35 40 45

Ala Thr Val Leu Arg Gln Phe Tyr Ser His His Glu Lys Asp Thr Arg
50 55 60

Cys Leu Gly Ala Thr Ala Gln Gln Phe His Arg His Lys Gln Leu Ile
65 70 75 80

Arg Phe Leu Lys Arg Leu Asp Arg Asn Leu Trp Gly Leu Ala Gly Leu
85 90 95

-continued

Asn Ser Cys Pro Val Lys Glu Ala Asn Gln Ser Thr Leu Glu Asn Phe
100 105 110

Leu Glu Arg Leu Lys Thr Ile Met Arg Glu Lys Tyr Ser Lys Cys Ser
115 120 125

Ser ( 2 ) INFORMATION FOR SEQ ID NO:3:

( i ) SEQUENCE CHARACTERISTICS:
( A ) LENGTH: 133 amino acids
( B ) TYPE: amino acid
( C ) STRANDEDNESS: unknown
( D ) TOPOLOGY: unknown ( i i ) MOLECULE TYPE: protein ( i x ) FEATURE:
( A ) NAME/KEY: Protein
( B ) LOCATION: 1..133
( D ) OTHER INFORMATION: /label= IL2

( x i ) SEQUENCE DESCRIPTION: SEQ ID NO:3:

Ala Pro Thr Ser Ser Ser Thr Lys Lys Thr Gln Leu Gln Leu Glu His
1 5 10 15

Leu Leu Leu Asp Leu Gln Met Ile Leu Asn Gly Ile Asn Asn Tyr Lys
20 25 30

Asn Pro Lys Leu Thr Arg Met Leu Thr Phe Lys Phe Tyr Met Pro Lys
35 40 45

Lys Ala Thr Glu Leu Lys His Leu Gln Cys Leu Glu Glu Glu Leu Lys
50 55 60

Pro Leu Glu Glu Val Leu Asn Leu Ala Gln Ser Lys Asn Phe His Leu
65 70 75 80

Arg Pro Arg Asp Leu Ile Ser Asn Ile Asn Val Ile Val Leu Glu Leu
85 90 95

Lys Gly Ser Glu Thr Thr Phe Met Cys Glu Tyr Ala Asp Glu Thr Ala
100 105 110

Thr Ile Val Glu Phe Leu Asn Arg Trp Ile Thr Phe Cys Gln Ser Ile
115 120 125

Ile Ser Thr Leu Thr
130

( 2 ) INFORMATION FOR SEQ ID NO:4:

( i ) SEQUENCE CHARACTERISTICS:
( A ) LENGTH: 127 amino acids
( B ) TYPE: amino acid
( C ) STRANDEDNESS: unknown
( D ) TOPOLOGY: unknown ( i i ) MOLECULE TYPE: protein ( i x ) FEATURE:
( A ) NAME/KEY: Protein
( B ) LOCATION: 1..127
( D ) OTHER INFORMATION: /label= GM- CSF ( x i ) SEQUENCE DESCRIPTION: SEQ ID NO:4:

Ala Pro Ala Arg Ser Pro Ser Pro Ser Thr Gln Pro Trp Glu His Val
1 5 10 15

Asn Ala Ile Gln Glu Ala Arg Arg Leu Leu Asn Leu Ser Arg Asp Thr
20 25 30

Ala Ala Glu Met Asn Glu Thr Val Glu Val Ile Ser Glu Met Phe Asp
35 40 45

-continued

Leu Gln Glu Pro Thr Cys Leu Gln Thr Arg Leu Glu Leu Tyr Lys Gln
50 55 60

Gly Leu Arg Gly Ser Leu Thr Lys Leu Lys Gly Pro Leu Thr Met Met
65 70 75 80

Ala Ser His Tyr Lys Gln His Cys Pro Pro Thr Pro Glu Thr Ser Cys
85 90 95

Ala Thr Gln Thr Ile Thr Phe Glu Ser Phe Lys Glu Asn Leu Lys Asp
100 105 110

Phe Leu Leu Val Ile Pro Phe Asp Cys Trp Glu Pro Val Gln Glu
115 120 125

( 2 ) INFORMATION FOR SEQ ID NO:5:

( i ) SEQUENCE CHARACTERISTICS:
( A ) LENGTH: 174 amino acids
( B ) TYPE: amino acid
( C ) STRANDEDNESS: unknown
( D ) TOPOLOGY: unknown ( i i ) MOLECULE TYPE: protein ( i x ) FEATURE:
( A ) NAME/KEY: Protein
( B ) LOCATION: 1..174
( D ) OTHER INFORMATION: /label= G- CSF ( x i ) SEQUENCE DESCRIPTION: SEQ ID NO:5:

Thr Pro Leu Gly Pro Ala Ser Ser Leu Pro Gln Ser Phe Leu Leu Lys
1 5 10 15

Cys Leu Glu Gln Val Arg Lys Ile Gln Gly Asp Gly Ala Ala Leu Gln
20 25 30

Glu Lys Leu Cys Ala Thr Tyr Lys Leu Cys His Pro Glu Glu Leu Val
35 40 45

Leu Leu Gly His Ser Leu Gly Ile Pro Trp Ala Pro Leu Ser Ser Cys
50 55 60

Pro Ser Gln Ala Leu Gln Leu Ala Gly Cys Leu Ser Gln Leu His Ser
65 70 75 80

Gly Leu Phe Leu Tyr Gln Gly Leu Leu Gln Ala Leu Glu Gly Ile Ser
85 90 95

Pro Glu Leu Gly Pro Thr Leu Asp Thr Leu Gln Leu Asp Val Ala Asp
100 105 110

Phe Ala Thr Thr Ile Trp Gln Gln Met Glu Glu Leu Gly Met Ala Pro
115 120 125

Ala Leu Gln Pro Thr Gln Gly Ala Met Pro Ala Phe Ala Ser Ala Phe
130 135 140

Gln Arg Arg Ala Gly Gly Val Leu Val Ala Ser His Leu Gln Ser Phe
145 150 155 160

Leu Glu Val Ser Tyr Arg Val Leu Arg His Leu Ala Gln Pro
165 170

( 2 ) INFORMATION FOR SEQ ID NO:6:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:6:

AATACGACTC ACTATAG 17

-continued ( 2 ) INFORMATION FOR SEQ ID NO:7:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:7:

GGCACCGTTG CGAATCCGGC CGCG 24

( 2 ) INFORMATION FOR SEQ ID NO:8:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:8:

TGCTTTACGG GCTACGCCCA GGACCAG 27

( 2 ) INFORMATION FOR SEQ ID NO:9:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:9:

GGGACCTCCG GACGATTTGC CTGAGGAGAC GGTGACCTCG GTACCTTGGC CCCAGTA 57

( 2 ) INFORMATION FOR SEQ ID NO:10:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:10:

GGGACCTCCA GCTTTACTCT CGAGCTTTGT CCCCGA 36

( 2 ) INFORMATION FOR SEQ ID NO:11:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:11:

CACCGTCCAG TTCTGCGTGC C 21

( 2 ) INFORMATION FOR SEQ ID NO:12:

( i ) SEQUENCE CHARACTERISTICS:

-continued ( A ) LENGTH: 21 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:12:

ATACGACTCA CTATAGGGAG A 21

( 2 ) INFORMATION FOR SEQ ID NO:13:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:13:

GGGCATAAAC CCGGGCATAA AACGCATGCA CCTACTTCAA GTTCTACAAA G 51

( 2 ) INFORMATION FOR SEQ ID NO:14:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:14:

TCAAGCTGAA TTCTAGGTGA GTGTTGAGAT GATGCTTTGA CA 42

( 2 ) INFORMATION FOR SEQ ID NO:15:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:15:

CGGCCACGAT GCGTCCGGCG T 21

( 2 ) INFORMATION FOR SEQ ID NO:16:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:16:

GGGCTTGGAT CCCCCCCCAC CTGAACCTCC TCCCCCGCTC GAACACTTTG AATATTT 57

( 2 ) INFORMATION FOR SEQ ID NO:17:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:17:

GAGGTCGGAT CCGGCGGAGG CGGATCTGGC GGAGGTGGCT CGGGCGGCAG CCTGGCCGCG 60

( 2 ) INFORMATION FOR SEQ ID NO:18:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:18:

TGTTGCTCCG GAGGTAACGG TGGGCACAAG TGCGATATCA CC 42

( 2 ) INFORMATION FOR SEQ ID NO:19:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:19:

CTTGTGCCCA CCGTTACCTC CGGACGAACA CTTTGAATAT TTCTC 45

( 2 ) INFORMATION FOR SEQ ID NO:20:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:20:

CTCAGTTGAA GCTTTGGAGG CAGCAAAGAT GTC 33

( 2 ) INFORMATION FOR SEQ ID NO:21:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:21:

TTTGCTGCCC ATATGAACAC AACTGAGAAG GAA 33

( 2 ) INFORMATION FOR SEQ ID NO:22:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:22:

ACTCTGGTAA GCTTCCTTCA CAGGACAGGA 30

( 2 ) INFORMATION FOR SEQ ID NO:23:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:23:

CCTGTGAAGC ATATGAACCA GAGTACGTTG GAAAAC 36

( 2 ) INFORMATION FOR SEQ ID NO:24:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:24:

TATTCAAAGT AAGCTTCCGG GGGAGGAGGT TCA 33

( 2 ) INFORMATION FOR SEQ ID NO:25:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:25:

GGAGATATAC ATATGGACAC AACTGAGAAG GAA 33

( 2 ) INFORMATION FOR SEQ ID NO:26:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:26:

GTTTAACTTT AAGCTTCCGG AGGTCCCGAG GACACAACTG AGAAGGAA 48

( 2 ) INFORMATION FOR SEQ ID NO:27:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:27:

CTCGGGACCT CGAGCTCATT TGGAGGCAGC AAAGAT 36

( 2 ) INFORMATION FOR SEQ ID NO:28:

( i ) SEQUENCE CHARACTERISTICS:

( A ) LENGTH: 42 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:28:

ACACTCACCG GAGGTAACGG TGGGGCACCT ACTTCAAGTT CT 42

( 2 ) INFORMATION FOR SEQ ID NO:29:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:29:

AAACTGAATT CAAGCTTACC TGGTGAGTTT GGGATT 36

( 2 ) INFORMATION FOR SEQ ID NO:30:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:30:

AAACTCACCC ATATGCTCAC ATTTAAGTTT 30

( 2 ) INFORMATION FOR SEQ ID NO:31:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:31:

AGGTGCCCCA CCGTTACCTC CGGTGAGTGT TGAGATGAT 39

( 2 ) INFORMATION FOR SEQ ID NO:32:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:32:

GAGGGCGGAG GAAACGGAGG TGGGGCACCC GCCCGCTCGC CC 42

( 2 ) INFORMATION FOR SEQ ID NO:33:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear -continued ( i i ) MOLECULE TYPE: DNA (primer)

( x i ) SEQUENCE DESCRIPTION: SEQ ID NO:33:

TTCTAGAATT CAAGCTTACT CAGCAGCAGT GTCTCT 36

( 2 ) INFORMATION FOR SEQ ID NO:34:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:34:

ACTGCTGCTC ATATGGATGA AACAGTAGAA GTC 33

( 2 ) INFORMATION FOR SEQ ID NO:35:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:35:

GGGTGCCCCA CCTCCGTTTC CTCCGCCCTC CTGGACTGGC TCCCA 45

( 2 ) INFORMATION FOR SEQ ID NO:36:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:36:

GCCTGCAGCC ATATGGCACC CGCCCGCTCG CCCAGCCCC 39

( 2 ) INFORMATION FOR SEQ ID NO:37:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:37:

CTCATGAATT CAAGCTTACT CCTGGACTGG CTCCCAGCAG TC 42

( 2 ) INFORMATION FOR SEQ ID NO:38:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:38:

AATTCAAGCT TCACGTGTGA GTTTGGGATT CTT 33

( 2 ) INFORMATION FOR SEQ ID NO:39:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:39:

AATTCAAGAA GCTTCTGCAG CAGTGTCTCT ACT 33

( 2 ) INFORMATION FOR SEQ ID NO:40:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:40:

CTGTGCACCC ATATGACCGT AACAGACATC 30

( 2 ) INFORMATION FOR SEQ ID NO:41:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:41:

GATGTCGTAA GCTTTCAACT CGGTGCACAG 30

( 2 ) INFORMATION FOR SEQ ID NO:42:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:42:

ACAGTGCAGC ATATGACCCC CCTGGGCCCT GCCAGC 36

( 2 ) INFORMATION FOR SEQ ID NO:43:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:43:

AATCTAAGCT TGGGGCTGGG CAAGGTGGCG TAG 33

( 2 ) INFORMATION FOR SEQ ID NO:44:

( i ) SEQUENCE CHARACTERISTICS:

( A ) LENGTH: 42 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:44:

GGGGGCGGAG GAAACGGAGG TGGGACCCCC CTGGGCCCTG CC 42

( 2 ) INFORMATION FOR SEQ ID NO:45:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:45:

CTGCAAAGCT TGGCTGGGGC AGCTGCT 27

( 2 ) INFORMATION FOR SEQ ID NO:46:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:46:

TGCCCCAGCC ATATGCTGCA GCTGGCAGGC TGC 33

( 2 ) INFORMATION FOR SEQ ID NO:47:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:47:

GGTCCCACCT CCGTTTCCTC CGCCGGGCTG GGCAAGGTGG CG 42

( 2 ) INFORMATION FOR SEQ ID NO:48:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:48:

TGGCGCGGTT TCTATATCGC C 21

( 2 ) INFORMATION FOR SEQ ID NO:49:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:49:

GGCCGGTCGC GGGAATTCTT AGAGCTCGTC TTTCGGCGGT TTGCCGGG 48

( 2 ) INFORMATION FOR SEQ ID NO:50:

( i ) SEQUENCE CHARACTERISTICS:
( A ) LENGTH: 5 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:50:

Gly Gly Asn Gly Gly
1 5

( 2 ) INFORMATION FOR SEQ ID NO:51:

( i ) SEQUENCE CHARACTERISTICS:
( A ) LENGTH: 5 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:51:

Ser Gly Gly Pro Glu
1 5

( 2 ) INFORMATION FOR SEQ ID NO:52:

( i ) SEQUENCE CHARACTERISTICS:
( A ) LENGTH: 7 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:52:

Gly Gly Gly Asn Gly Gly Gly
1 5

( 2 ) INFORMATION FOR SEQ ID NO:53:

( i ) SEQUENCE CHARACTERISTICS:
( A ) LENGTH: 6 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:53:

Arg Pro His Met Ala Asp
1 5

( 2 ) INFORMATION FOR SEQ ID NO:54:

( i ) SEQUENCE CHARACTERISTICS:
( A ) LENGTH: 5 amino acids
( B ) TYPE: amino acid
( C ) STRANDEDNESS: unknown
( D ) TOPOLOGY: unknown ( i i ) MOLECULE TYPE: peptide -continued ( x i ) SEQUENCE DESCRIPTION: SEQ ID NO:54:

Gly Gly Gly Gly Ser
1 5

( 2 ) INFORMATION FOR SEQ ID NO:55:

( i ) SEQUENCE CHARACTERISTICS:
( A ) LENGTH: 20 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:55:

Gly Gly Gly Gly Ser Gly Gly Gly Gly Ser Gly Gly Gly Gly Ser Gly
1 5 10 15

Gly Gly Gly Ser
20

( 2 ) INFORMATION FOR SEQ ID NO:56:

( i ) SEQUENCE CHARACTERISTICS:
( A ) LENGTH: 22 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:56:

Ala Ser Gly Gly Gly Gly Ser Gly Gly Gly Gly Ser Gly Gly Gly Gly
1 5 10 15

Ser Gly Gly Gly Gly Ser
20

( 2 ) INFORMATION FOR SEQ ID NO:57:

( i ) SEQUENCE CHARACTERISTICS:
( A ) LENGTH: 6 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:57:

Ala Ser Gly Gly Pro Glu
1 5

FUSION PROTEINS COMPRISING CIRCULARLY PERMUTED LIGANDS

This invention relates to the production and use of circularly permuted ligands and fusions of two or more proteins where one of the proteins is circularly permuted.

BACKGROUND OF THE INVENTION

Fusion proteins are polypeptide chains consisting of two or more proteins fused together into a single polypeptide chain. If one of the proteins is a ligand, then the resulting ligand fusion proteins bind to cells bearing receptors specific for the particular ligand.

Where the first protein is a ligand and the second protein is a cytotoxin, the ligand fusion protein may act as a potent cell-killing agent specifically targeting the cytotoxin to cells bearing a particular receptor type. For example, chimeric fusion proteins which include interleukin 4 (IL4) or transforming growth factor (TGFα) fused to Pseudomonas exotoxin (PE) or interleukin 2 (IL2) fused to Diphtheria toxin (DT) have been tested for their ability to specifically target and kill cancer cells (Pastan et al., *Ann. Rev. Biochem.*, 61: 331–354 (1992)).

Alternatively, where the ligand is fused to another specific binding moiety such as an antibody, a growth factor, or another ligand, the fusion protein may act as a highly specific bifunctional linker. This linker may act to bind and enhance the interaction between cells or cellular components to which the fusion protein binds. Thus, for example, where the fusion protein is a growth factor joined to an antibody or antibody fragment (e.g. an Fv fragment of an antibody), the antibody may specifically bind antigen positive cancer cells while the growth factor binds receptors (e.g., IL2 or IL4 receptors) on the surface of immune cells. The fusion protein may thus act to enhance and direct an immune response toward target cancer cells.

Ligands are typically employed in fusion proteins to act as specific targeting moieties. Generally it is desirable to increase specificity and affinity and decrease cross-reactivity of the fusion protein to make it more effective. For example, native PE and DT are highly toxic compounds that typically bring about death through liver toxicity. PE and DT can be transformed into chimeric toxins by removing the native targeting component of the toxin and replacing it with a different specific targeting moiety (e.g. IL4 which targets cells bearing IL4 receptors). However, even these chimeric toxins show some non-specific binding. They attack the liver in addition to their target cells and, when given in large doses, may also produce death due to liver toxicity.

It has been observed that growth factors, and other targeting moieties, frequently show lower specificity and affinity for their targets when they are incorporated into fusion proteins. See, for example, Debinski, et al., *J. Biol. Chem.*, 268: 14065–14070 (1993); Lorberboum-Galski, et al., *J. Biol. Chem.*, 263: 18650–18656 (1988); Williams, et al., *J. Biol. Chem.*, 265: 11885–11889 (1990); and Edwards, et al. *Mol. Cell. Biol.*, 9: 2860–2867 (1989).

SUMMARY OF THE INVENTION

This invention provides novel modified forms of ligands such as interleukin 4 (IL4) wherein the amino and carboxy ends are joined together, directly or through a linker, and new amino and carboxy terminal ends are formed at a different location within the ligand. These modified ligands are as fully active as the original ligands. Since the modification of the ligand represents a rearrangement of the molecule, neither the function, nor the desirability of such molecules was apparent prior to the work described here. Such rearranged molecules are also referred to as circularly permuted proteins.

The circularly permuted ligands are especially useful when employed as a component in a fusion protein of interest. Oftentimes fusion of a protein to an original terminus of a ligand interferes with binding of the ligand to its native receptor. For example, fusing a toxin to the carboxy terminus of IL4 greatly interferes with the binding of IL4 to its receptor. Binding affinity of IL4 fusion proteins is greatly enhanced by the use of fusion proteins employing the circularly permuted IL4 molecules described here. It is believed that the reduced affinity in growth factor-toxin or other ligand-toxin fusion proteins is due, at least in part, to the inability of the targeting moiety to achieve its native conformation when incorporated into a fusion protein or to stearic hinderance between the active site of the targeting moiety and the fused protein. This invention overcomes these limitations providing novel ligands and ligand fusion proteins that have a binding specificity and affinity comparable to or greater than native ligand fusion proteins. Thus, a valuable use for circularly permuted ligands is disclosed here and it is shown that such functional permuted ligands may be effectively fused to proteins of interest, such as toxins.

consisted of Met followed by amino acids 105–129, GGNGG (Seq. Id. No. 50) and 1–104. For cloning purposes, each IL4 mutant contained alanine at the new C-terminus. This alaninc was residue 104 for IL4(105-104) and constituted an extra residue for IL4(38-37).

Figure 3A:
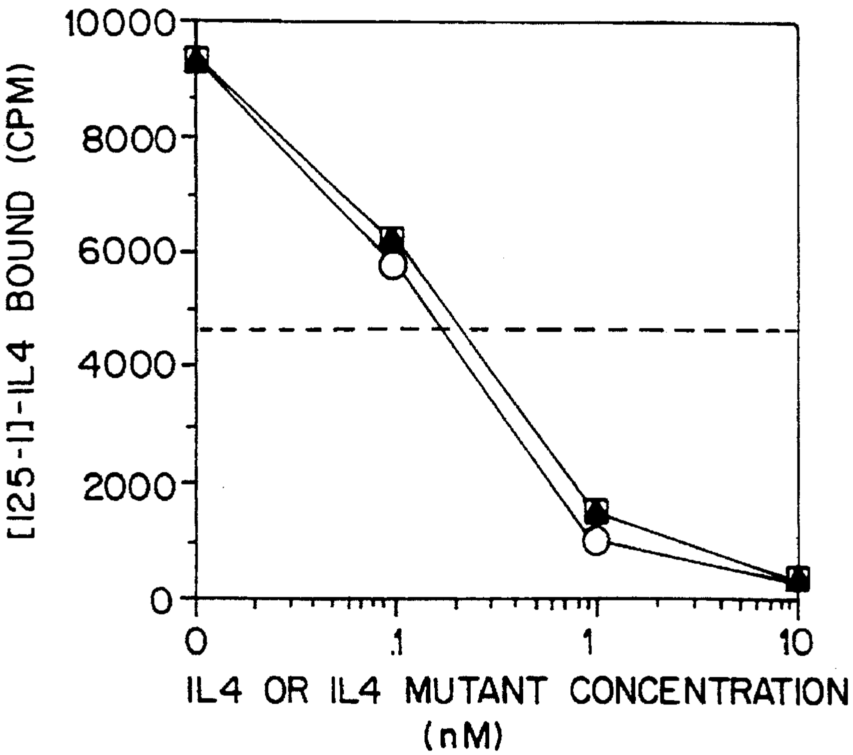

FIG. 3 shows the binding and proliferative activity of circularly permuted IL4 mutants. (A) Displacement analysis: Bound [$^{125}$I]-IL4 plotted as a function of IL4 (O), IL4(38-37) (▲) or IL4(105-104) (□) concentration. (B) Mitogen activity: [$^{3}$H]-thymidine incorporation by CTLL$^{hIL4R}$ cells plotted as a function of IL4(O), IL4(38-37) (▲) or IL4(105-105) (□) concentration. For A and B, the data is composed of the means of triplicate or quadruplicate experiments and error bars represent standard deviations from the mean.

FIG. 4 shows the binding and cytotoxic activity of circularly permuted IL4-PE fusion protein IL4(38-37)-PE38QQRDEL compared to the native IL4-PE fusion protein IL4-PE38QQRDEL. (A) Amount of ([$^{125}$I]-IL4) bound to DAUDI cells plotted as a function of the concentration of IL4(□), IL4(38-37)-PE38QQRDEL (●) or IL4-PE38QQRDEL (○) in the culture media. (B) Uptake of [$^{3}$H]-leucine by ATAC-4 cells in the presence of varying concentrations of IL4(38-37)-PE38QQRDEL (●) or IL4-PE38QQRDEL (○). Cells were also incubated with IL4(38-37)-PE38QQRDEL (▲) or IL4-PE38QQRDEL (Δ) each combined with an excess (10/μg/ml) of IL4. The $IC_{50}$'s, the concentrations needed for 50% inhibition of protein synthesis, were 0.24 and 0.75 ng/ml for IL4(38-37)-PE38QQRDEL and IL4-PE38QQRDEL, respectively.

DETAILED DESCRIPTION

Definitions

The term "circularly permuted" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The particular circular permutation of a molecule is designated by brackets containing the amino acid residues between which the peptide bond is eliminated. Thus, the designation IL4(105-104) designates a circularly permuted IL4 growth factor in which the opening site (position at which the peptide bond is eliminated) occurred between residues 105 and 104 of the unpermuted or unmodified IL4.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The terms "unpermuted," "native" or "unmodified" ligand, growth factor, or protein are used herein to provide a reference point for the ligand, growth factor or protein prior to its rearrangement into a circularly permuted molecule, as described above. Typically, the unmodified ligand, growth factor or protein has amino and carboxyl termini and an amino acid sequence that correspond substantially to the amino and carboxyl termini and amino acid sequence of the ligand, growth factor, or protein as it generally occurs in vivo. The unmodified ligand, growth factor, or protein however, may have a methionine at the amino terminus if produced as a non-secreted form.

The term "linker", as used herein, refers to a molecule that is used to join the amino and carboxyl termini of a protein. The linker is capable of forming covalent bonds to both the amino and carboxyl terminus. Suitable linkers are well known to those of skill in the art and include, but are not limited to, straight or branched-chain carbon linkers, heterocyclic carbon linkers, or peptide linkers. The linkers may be joined to the carboxyl and amino terminal amino acids through their side groups (e.g., through a disulfide linkage to cysteine). However, in a preferred embodiment, the linkers will be joined to the alpha carbon amino and carboxyl groups of the terminal amino acids.

A "ligand", as used herein, refers generally to all molecules capable of reacting with or otherwise recognizing or binding to a receptor on a target cell. Specifically, examples of ligands include, but are not limited to, antibodies, lymphokines, cytokines, receptor proteins such as CD4 and CD8, solubilized receptor proteins such as soluble CD4, hormones, growth factors, and the like which specifically bind desired target cells.

A "growth factor" as used herein refers to a protein ligand that stimulates cell division or differentiation or inhibits cell division or stimulates or inhibits a biological response like motility or secretion of proteins. Growth factors are well known to those of skill in the art and include, but are not limited to, platelet-derived growth factor (PDGF), epidermal growth factor (EGF), insulin-like growth factor (IGF), transforming growth factor β (TGF-β), fibroblast growth factors (FGF), interleukin 2 (IL2), nerve growth factor (NGF), interleukin 3 (IL3), interleukin 4 (IL4), interleukin 1 (IL1), interleukin 6 (IL6), interleukin 7 (IL7), granulocyte/macrophage colony-stimulating factor (GM-CSF), granulocyte colony-stimulating factor (G-CSF), macrophage colony-stimulating factor (M-CSF), erythropoietin and the like. One of skill in the art recognizes that the term growth factor as used herein generally includes cytokines and colony stimulating factors.

The term "residue" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

The term "opening site", as used herein when referring to circular permutation, refers to the position at which a peptide bond would be eliminated to form new amino and carboxyl termini. The opening site is designated by the positions of the pair of amino acids, located between the amino and carboxyl termini of the unpermuted (native) protein, that become the new amino and carboxyl termini of the circularly permuted protein. Where the unpermuted protein is J amino acids in length and its residues are numbered 1 through J from the amino to the carboxyl terminus, the opening site will be designated as between residues n and n+1 where n is an integer from 1 through J–1.

The term "antibody", as used herein, includes various forms of modified or altered antibodies, such as an intact immunoglobulin, an Fv fragment containing only the light and heavy chain variable regions, an Fv fragment linked by a disulfide bond (Brinkmann, et al. *Proc. Natl. Acad. Sci.*

*USA*, 90: 547–551 (1993)), an Fab or $(Fab)'_2$ fragment containing the variable regions and parts of the constant regions, a single-chain antibody and the like (Bird et al., *Science* 242: 424–426 (1988); Huston et al., *Proc. Nat. Acad. Sci. USA* 85: 5879–5883 (1988)). The antibody may be of animal (especially mouse or rat) or human origin or may be chimeric (Morrison et al., *Proc Nat. Acad. Sci. USA* 81: 6851–6855 (1984)) or humanized (Jones et al., *Nature* 321: 522–525 (1986), and published UK patent application #8707252). Methods of producing antibodies suitable for use in the present invention are well known to those skilled in the art and can be found described in such publications as Harlow & Lane, *Antibodies: A Laboratory Manual*, Cold Spring Harbor Laboratory (1988), and Asai, *Methods in Cell Biology* Vol. 37: *Antibodies in Cell Biology*, Academic Press, Inc. New York (1993).

The term "Pseudomonas exotoxin" (PE) as used herein refers to a full-length native (naturally occurring) PE or a PE that has been modified. Such modifications may include, but are not limited to, elimination of domain Ia, various amino acid deletions in domains II and III, single amino acid substitutions (e.g., replacing Lys with Gln at positions 590 and 606), and the addition of one or more sequences at the carboxyl terminus such as KDEL and REDL.

The term "Diphtheria toxin" (DT) as used herein refers to full length native DT or to a DT that has been modified. Modifications typically include removal of the targeting domain in the B chain and, more specifically, involve truncations of the carboxyl region of the B chain.

Native Pseudomonas exotoxin (PE), IL4, IL2, GM-CSF, and G-CSF have the amino acid sequences set forth in Sequence Id. Listings Nos. 1 through 5 respectively. All amino acid positions described herein use as a frame of reference these sequence listings. For example, a PE molecule "comprising amino acids 280 to 613" would refer to a molecule having amino acids substantially corresponding to those positions on Sequence Id. Listing No. 1. Other common references are used herein to indicate deletions or substitutions to a sequence using the respective native sequence Id. listing as a frame of reference. The use of the symbol "Δ" refers to a deletion of the amino acids following the symbol. For example, "Δ365–380", refers to the deletion from a PE molecule of amino acids 365 to 380. Amino acid substitutions may be indicated by parentheses, for example "(Ser 287)" refers to a molecule having serine at amino acid position 287. Circularly permuted molecules are designated by the native molecule followed by brackets enclosing the amino acid positions that comprise the opening site. Thus, for example, IL4(105-104) designates a circularly permuted IL4 in which the new termini are residues 105 and 104 of the unpermuted IL4. Amino acids are also sometimes referred to here by the single letter codes recommended by the IUPAC-IUB Biochemical Nomenclature commission. It is, of course, recognized that some substitutions, addition, or deletions may be made to any sequences described herein that do not alter the biological activity of the region. Indeed, some such modifications may be required to achieve expression of a particular protein. Thus, for example, a methionine may be added to a sequence to provide an initiator.

The present invention provides for circularly permuted ligands which possess specificity and binding affinity comparable to or greater than the specificity and binding affinity of the native (unpermuted) ligand.

The present invention also provides for novel fusion proteins comprising at least one circularly permuted ligand fused to one or more second protein(s) of interest which may be, for example, a cytotoxin, an antibody, a ligand, a hormone, a growth factor, a circularly permuted ligand, a circularly permuted hormone, or a circularly permuted growth factor. The first circularly permuted ligand acts to target and bind the fusion protein to particular cells or cellular components where the second protein may exercise its characteristic activity.

In a number of ligands (e.g. growth factors and other proteins), the carboxyl and amino termini are situated relatively close to the active site when the protein is folded into its native conformation. When fusion proteins are formed by joining a second protein to either terminus of the first protein, specificity, binding affinity, or other activities of the fused first protein may be decreased relative to the unfused first protein presumably due to altered folding caused by the presence of the added protein component or to stearic hinderance between the second protein component and the active site of the first protein component.

Circular permutation of the molecule as described here provides a means by which the first protein may be altered to produce new carboxyl and amino termini without diminishing the specificity and binding affinity of the altered first protein relative to its native form. With new termini located away from the active site, it is possible to incorporate the circularly permuted first proteins into fusion proteins with a smaller or no diminution of activity of the first protein.

Circularly permuted proteins, which include DNA, RNA and protein, are single-chain molecules which have their normal termini fused, often with a linker, and contain new termini at another position. See Goldenberg, et al. *J. Mol. Biol.*, 165: 407–413 (1983) and Pan et al. *Gene* 125: 111–114 (1993), both incorporated by reference herein. Circular permutation is functionally equivalent to taking a straight-chain molecule, fusing the ends to form a circular molecule, and then cutting the circular molecule at a different location to form a new straight chain molecule with different termini. Circular permutation thus has the effect of essentially preserving the sequence and identity of the amino acids of a protein while generating new termini at different locations.

Figure 1A:
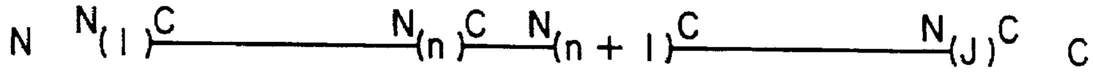
FIG. 1 schematically illustrates the circular permutation of a linear polymer (e.g., a protein). (A) An unpermuted (native) linear protein of length J in which the amino acid residues are numbered sequentially from the amino to the carboxyl terminus from 1 to J. A pair of adjacent amino acids will be numbered n and n+1 respectively where n is an integer ranging from 1 to J–1. The "N" and "C" superscripts on these residues indicates the orientation of the alpha carbon amino and carboxyl groups in each amino acid. (B) The protein of (A) has been circularized by joining the amino and carboxyl termini with a linker (double lines). The circularized protein is then opened at an opening site between the original amino and carboxyl terminal amino acids. The location of the opening site is between adjacent residues n and n+1. (C) Elimination of the peptide bond between residues n and n+1 produces a free alpha carbon carboxyl group on residue n and a free alpha carbon amino group on residue n+1. Thus, these residues become the new carboxyl and amino termini respectively. Proceeding from the amino to the carboxyl terminus, the protein thus comprises a sequence corresponding essentially to the amino acid sequence of residues n+1 through J of the protein in (a) followed by the linker, followed by a sequence corresponding essentially to the amino acid sequence of residues 1 through n of the protein in (a).
Figure 1B:
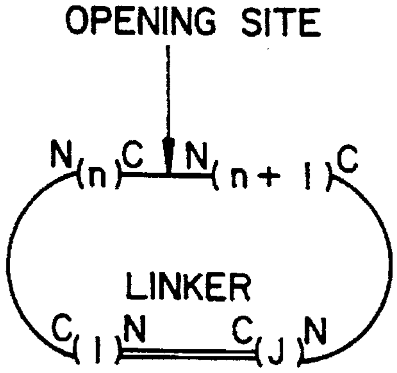
Figure 1C:

The process of circular permutation is schematically illustrated in FIG. 1. FIG. 1(A) illustrates an unpermuted linear polymeric molecule (in this case a protein) J subunits in length. The constituent amino acid residues are numbered sequentially 1 through J from the amino to the carboxyl terminus. A pair of adjacent amino acids within this protein may be numbered n and n+1 respectively where n is an integer ranging from 1 to J–1. To circularly permute the protein, the amino and carboxyl termini are first joined by a linker producing a circular molecule (FIG. 1(B)). A new linear molecule is formed by cutting or opening the circular molecule at any location between amino acid residues 1 and J. Thus, the location of the opening site, illustrated by the arrow in FIG. 1(B) may be designated as between amino acid residues n and n+1. Elimination of the peptide bond between residue n and n+1 will produce a free alpha carbon amino group on residue n+1 and a free alpha carbon carboxyl group on residue n. These residues become the new amino and carboxyl termini respectively (FIG. 1(C)). Thus, circular permutation produces a new linear protein which, proceeding from the amino to the carboxyl terminus, comprises the segment of the original protein corresponding to residues n+1 through J followed by the linker, followed by a segment of the original protein corresponding to residues 1 through n (FIG. 1(C)).

It will be appreciated that while circular permutation is described in terms of linking the two ends of a protein and then cutting the circularized protein these steps are not actually required to create the end product. A protein synthesized de novo with the sequence illustrated by FIG. 1(C) would be equivalent to a protein made by circularization and cutting. Thus, circularized permutations of a generic protein illustrated by FIG. 1(A) refers to all refers to all proteins of FIG. 1(C) structure regardless of how they are constructed.

It is important to create a permutation that will retain the biological activity of the native form of the molecule. If the new termini interrupt a critical region of the native protein, activity may be lost. Similarly, if linking the original termini destroys activity, then no permutation will retain biological activity. Thus, there are two requirements for the creation of an active circularly permuted protein: 1) The termini in the native protein must be favorably located so that creation of a linkage does not destroy biological activity; and 2) There must exist an "opening site" where new termini can be formed without disrupting a region critical for protein folding and desired biological activity.

Thus, in general, good candidates for circular permutation are proteins in which the termini of the original protein are in close proximity and favorably oriented. Where the termini are naturally situated close together, it is expected that direct fusion of the termini to each other or introduction of a linker will have relatively little effect. It has been suggested that in roughly one third of the known structures of globular proteins the termini are in relatively close proximity (Thorton et al. *J. Mol. Biol.,* 167: 443–460 (1983)). However, because the linker may be of any length, close proximity of the native termini is not an absolute requirement.

In a preferred embodiment, it is desirable to use a linker that preserves the spacing between the termini comparable to the unpermuted or native molecule. Generally linkers are either hetero- or homo-bifunctional molecules that contain two reactive sites that may each form a covalent bond with the carboxyl and the amino terminal amino acids respectively. Suitable linkers are well known to those of skill in the art and include, but are not limited to, straight or branched-chain carbon linkers, heterocyclic carbon linkers, or peptide linkers. The most common and simple example is a peptide linker that typically consists of several amino acids joined through peptide bonds to the termini of the native protein. The linkers may be joined to the terminal amino acids through their side groups (e.g., through a disulfide linkage to cysteine). However, in a preferred embodiment, the linkers will be joined through peptide bonds to the alpha carbon amino and carboxyl groups of the terminal amino acids.

Functional groups capable of forming covalent bonds with the amino and carboxyl terminal amino acids are well known to those of skill in the art. For example, functional groups capable of binding the terminal amino group include anhydrides, carbodimides, acid chlorides, activated esters and the like. Similarly, functional groups capable of forming covalent linkages with the terminal carboxyl include amines, alcohols, and the like. In a preferred embodiment, the linker will itself be a peptide and will be joined to the protein termini by peptide bonds. For example, the termini of the growth factor IL4 are normally spaced about 11.2 Å apart (Powers et al. *Biochem,* 32: 6744–6762 (1993). A preferred linker that essentially preserves this spacing is the peptide GGNGG (Seq. Id. No. 50). Similarly, a preferred linker for circularly permuted G-CSF and GM-CSF is GGGNGGG (Seq. Id. No. 52).

Circular permutation requires that the protein have an opening site (i.e., between residues n and n+1) where the formation of termini will not interrupt secondary structure crucial in the folding process or critical elements of the final conformation. Even if the three-dimensional structure is compatible with joining the termini, it is conceivable that the kinetics and thermodynamics of folding would be greatly altered by circular permutation if opening the circularized protein separates residues that participate in short range interactions crucial for the folding mechanism or the stability of the native state. Goldenberg, *Protein Eng.,* 7: 493–495 (1989). Thus, the choice of an opening site is important to the protein activity.

The selection of an opening site may be determined by a number of factors. Where the three dimensional conformation of the protein is known or predicted, preferred opening sites will be located in regions that do not show a highly regular three-dimensional structure. Thus, it is preferred that opening sites be selected in regions of the protein that do not show secondary structure such as alpha helices, pleated sheets, oeB barrel structures, and the like.

Methods of identifying regions of particular secondary structure based on amino acid sequence are widely known to those of skill in the art. See, for example, Cohen et al., *Science,* 263: 488–489 (1994), incorporated by reference herein. Numerous programs exist that predict protein folding based on sequence data. Some of the more widely known software packages include MatchMaker (Tripos Associates, St. Louis, Mo., U.S.A.), FASMAN from GCG (Genetics Computer Group), PHD (European Molecular Biology Laboratory, Heidelburg, Germany) and the like.

Alternatively, where the substitution of certain amino acids or the modification of the side chains of certain amino acids does not change the activity of a protein, it is expected that the modified amino acids are not critical to the protein's activity. Thus, amino acids that are either known to be susceptible to modification or are actually modified in vivo are potentially good candidates for opening sites. For example, residues 38 and 105 of IL4 are potential glycosylation sites (Carret al., *Biochem,* 80: 1515–111523 (1991), Powers et al., *Science* 256: 1673–1677 (1992)). Glycosylation of residue 38 in IL4 does not change the binding specificity or affinity of IL4 for its target receptors. Thus residues 38 and 105 are potentially good candidates for opening sites.

Where the protein is a member of a family of related proteins, one may infer that the highly conserved sequences are critical for biological activity, while the variable regions are not. Preferred opening sites are then selected in regions of the protein that do not show highly conserved sequence identity between various members of the protein family. Alternatively, if an opening site is identified in a conserved region of a protein, that same region provides a good candidate for opening sites in a homologous protein.

Methods of determining sequence identity are well known to those of skill in the art. Sequence comparisons between two (or more) polynucleotides or polypeptides are typically performed by comparing regions of the two sequences over a "comparison window" to identify and compare local regions of sequence similarity. Since the goal is to identify very local sequence regions that are not conserved, the comparison window will be selected to be rather small. A "comparison window", as used herein, refers to a segment of at least about 5 contiguous positions, usually about 10 to about 50, more usually about 15 to about 40 in which a sequence may be compared to a reference sequence of the same number of contiguous positions after the two sequences are optimally aligned.

Optimal alignment of sequences for comparison may be conducted by the local homology algorithm of Smith et al. *Adv. Appl. Math.* 2: 482 (1981), by the homology alignment algorithm of Needleman et al., *J. Mol. Biol.* 48:443 (1970), by the search for similarity method of Pearson et al., *Proc. Natl. Acad. Sci. USA,* 85: 2444 (1988), by computerized implementations of these algorithms (GAP, BESTFIT, FASTA, and TFASTA in the Wisconsin Genetics Software Package, Genetics Computer Group (GCG), 575 Science Dr., Madison, Wis., U.S.A.), or by inspection.

Preferred opening sites in IL4 are between residues 37 and 38 and between residues 104 and 105. A preferred opening site in IL2 is between residues 39 and 38, while preferred opening sites in GM-CSF and G-CSF are between residues 36 and 35 and between residues 69 and 68 respectively.

Circularly permuted proteins may be made by a number of means known to those of skill in the art. These include chemical synthesis, modification of existing proteins, and expression of circularly permuted proteins using recombinant DNA methodology.

Where the protein is relatively short (i.e., less than about 50 amino acids) the circularly permuted protein may be synthesized using standard chemical peptide synthesis techniques. If the linker is a peptide it may be incorporated during the synthesis. If the linker is not a peptide it may be coupled to the peptide after synthesis. Solid phase synthesis in which the C-terminal amino acid of the sequence is attached to an insoluble support followed by sequential addition of the remaining amino acids in the sequence is the preferred method for the chemical synthesis of the circularly permuted ligands and fusion proteins of this invention. Techniques for solid phase synthesis are described by Barany and Merrifield, *Solid-Phase Peptide Synthesis*; pp. 3–284 in *The Peptides: Analysis, Synthesis, Biology*. Vol. 2: *Special Methods in Peptide Synthesis*, Part A., Merrifield, et al. *J. Am. Chem. Soc.*, 85: 2149–2156 (1963), and Stewart et al., *Solid Phase Peptide Synthesis,* 2nd ed. Pierce Chem. Co., Rockford, Ill. (1984) which are incorporated herein by reference.

Alternatively, the circularly permuted protein may be made by chemically modifying a native protein. Generally, this requires reacting the native protein in the presence of the linker to form covalent bonds between the linker and the carboxyl and amino termini of the protein, thus forming a circular protein. New termini are then formed by opening the peptide bond joining amino acids at another location. This may be accomplished chemically or enzymatically using, for example, a peptidase.

If the opening reaction tends to hydrolyze more than one peptide bond, the reaction may be run briefly. Those molecules having more than one peptide bond opened will be shorter than the full length circularly permuted molecule and the latter may be isolated by any protein purification technique that selects by size (e.g., by size exclusion chromatography or electrophoresis). Alternatively, various sites in the circular protein may be protected from hydrolysis by chemical modification of the amino acid side chains which may interfere with enzyme binding, or by chemical blocking of the vulnerable groups participating in the peptide bond.

In a preferred embodiment, the circularly permuted protein, or fusion proteins comprising the circularly permuted protein will be synthesized using recombinant DNA methodology. Generally this involves creating a DNA sequence that encodes the circularly permuted ligand (or entire fusion protein containing the ligand), placing the DNA in an expression cassette under the control of a particular promoter, expressing the protein in a host, isolating the expressed protein and, if required, renaturing the protein.

DNA encoding circularly permuted ligands or fusion proteins comprising circularly permuted ligands may be prepared by any suitable method, including, for example, cloning and restriction of appropriate sequences or direct chemical synthesis by methods such as the phosphotriester method of Narang et al. *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.,* 22: 1859–1862 (1981); and the solid support method of U.S. Pat. No. 4,458,066, all incorporated by reference herein.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, sub sequences may be cloned and the appropriate subsequences cleaved using appropriate restriction enzymes. The fragments may then be ligated to produce the desired DNA sequence.

In a preferred embodiment, DNA encoding the circularly permuted ligand may be produced using DNA amplification methods, for example polymerase chain reaction (PCR). First, the segments of the native DNA on either side of the new terminus are amplified separately. For example, since the native protein sequence of IL4 is 129 amino acids long and the opening site is between amino acids 37 and 38 respectively, the sequences representing codons 1 through 37 and 38 through 129 are amplified separately. The 5' end of the first amplified sequence encodes the peptide linker, while the 3' end of the second amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons 38–129, the linker, and codons 1–37. The circularly permuted molecule may then be ligated into a plasmid.

The circularly permuted ligands and their fusion proteins may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, *R. Scopes, Protein Purification*, Springer-Verlag, New York (1982), Deutscher, *Methods in Enzymology* Vol. 182: *Guide to Protein Purification.*, Academic Press, Inc. New York (1990)). Substantially pure compositions of at least about 90 to 95 % homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the circularly permuted growth-factor or a fusion protein comprising a circularly permuted growth-factor may possess a conformation substantially different than the native protein. In this case, it may be necessary to denature and reduce the protein and then to cause the protein to re-fold into the preferred conformation. Methods of reducing and denaturing the protein and inducing re-folding are well known to those of skill in the art. (See, Debinski et al. *J. Biol. Chem.,* 268: 14065–14070 (1993); Kreitman and Pastan, *Bioconjug. Chem.,* 4: 581–585 (1993); and Buchner, et al., *Anal. Biochem,* 205: 263–270 (1992) which are incorporated herein by reference.) Debinski et al., for example, describe the denaturation and reduction of inclusion body proteins in guanidine-DTE. The protein is then refolded in a redox buffer containing oxidized glutathione and L-arginine.

One of skill would recognize that modifications can be made to the circularized protein without diminishing its biological activity. Some modifications may be made to facilitate the cloning, expression, or incorporation of the circularly permuted ligand into a fusion protein. Such modifications are well known to those of skill in the art and include, for example, a methionine added at the amino terminus to provide an initiation site, or additional amino acids placed on either terminus to create conveniently located restriction sites or termination codons. For example, in a preferred embodiment, circularly permuted IL4 will have an additional methionine (Met) at the amino terminus to provide an initiation site. For cloning purposes, each IL4 mutant will contain alaninc at the new C-terminus. This alanine is residue 104 for IL4(105-104) and constitutes an additional residue for IL4(38-37).

One of skill will recognize that other modifications may be made. Thus, for example, amino acid substitutions may be made that increase specificity or binding affinity of the circularly permuted protein, etc. Alternatively, non-essential regions of the molecule may be shortened or eliminated entirely. Thus, where there are regions of the molecule that are not themselves involved in the activity of the molecule, they may be eliminated or replaced with shorter segments that merely serve to maintain the correct spatial relationships between the active components of the molecule.

This invention provides for fusion proteins comprising a circularly permuted ligand joined to another protein such as an antibody, an antibody fragment (e.g. anti-Tac(Fv)), a hormone, an enzyme, a releasing factor, a ligand, a growth factor, a circularly permuted growth factor, or another circularly permuted ligand. The two proteins may be fused together directly or joined by means of a peptide spacer. The peptide spacer may range from about 1 to 40 residues in length. In one preferred embodiment, the circularly permuted ligand is a growth factor.

Generally, the spacer has no biological activity itself and functions only to link and provide some distance between the two active proteins comprising the fusion protein. However, one of skill will recognize that the residues of the spacer may be chosen to optimize a property of the fusion protein. For example, a spacer containing hydrophobic amino acids may enhance the solubility of the fusion protein in various lipids, while polar or charged residues in the spacer may enhance solubility in aqueous solutions. Similarly, the spacer residues may be chosen for their effect on the folding of the fusion protein. Where the fusion protein comprises a circularly permuted IL4, IL2, GM-CSF, or G-CSF joined to a Pseudomonas exotoxin a preferred peptide spacer is SGGPE (Seq. Id. No. 51). Where the fusion protein comprises a circularly permuted IL4 joined to Diptheria toxin DT388 preferred spacers are HM or RPHMAD (Seq. Id. No. 53). Where the fusion protein comprises circularly permuted IL4 joined to an B3(Fv), a preferred spacer is ASGGPE (Seq. Id. No. 57).

Chimeric toxin fusion proteins are of particular interest and comprise a circularly permuted ligand fused to a toxin. One of skill in the art would recognize that many toxins are suitable including Pseudomonas exotoxin, Diphtheria toxin, other bacterial toxins, and derivatives of plant or animal toxins. In a preferred embodiment, the fusion protein comprises a circularly permuted growth-factor fused to either a Pseudomonas exotoxin or a Diphtheria toxin.

Pseudomonas exotoxin A (PE) is an extremely active monomeric protein (molecular weight 66 kD), secreted by Pseudomonas aeruginosa, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1–252) mediates cell binding. Domain II (amino acids 253–364) is responsible for translocation into the cytosol and domain III (amino acids 400–613) mediates ADP ribosylation of elongation factor 2, which inactivates the protein and causes cell death. The function of domain Ib (amino acids 365–399) remains undefined, although a large part of it, amino acids 365–380, can be deleted without loss of cytotoxicity. See Siegall et al., *J. Biol. Chem.* 264: 14256–14261 (1989), incorporated by reference herein. For example, in the case of B3(Fv)PE38 (described below), residues 350 to 394 can be deleted and if replaced with GGGGS (Seq. Id. No. 54) are fully active.

Where the circularly permuted ligand is fused to PE, a preferred PE molecule is one in which domain Ia (amino acids 1 through 252) is deleted and amino acids 365 to 380 have been deleted from domain lb. However all of domain lb and a portion of domain II (amino acids 350 to 394) can be deleted, particularly if the deleted sequences are replaced with a linking peptide such as GGGGS (Seq. Id. No. 54).

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, REDLK (as in native PE), REDL, RDEL, or KDEL, repeats of those, or other sequences that function to maintain or recycle proteins into the endoplasmic reticulum, referred to here as "endoplasmic retention sequences". See, for example, Chaudhary et al, *Proc. Natl. Acad. Sci. USA* 87:308–312 and Seetharam et al, *J. Biol. Chem.* 266: 17376–17381 (1991) and commonly assigned, U.S. Ser. No. 07/459,635 filed Jan. 2, 1990, now abandoned, all of which are incorporated by reference herein.

Deletions of amino acids 365–380 of domain Ib can be made without loss of activity. Further, a substitution of methionine at amino acid position 280 in place of glycine to allow the synthesis of the protein to begin and of serine at amino acid position 287 in place of cysteine to prevent formation of improper disulfide bonds is beneficial. In a preferred embodiment, the circularly permuted ligand is inserted in replacement for domain Ia. A similar insertion has been accomplished in what is known as the TGFα/PE40 molecule (also referred to as TP40) described in Heimbrook et al., *Proc. Natl. Acad. Sci., USA,* 87: 4697–4701 (1990) and in commonly assigned U.S. Ser. No. 07/865,722 filed Apr. 8, 1992, pending and in U.S. Ser. No. 07/522,563 filed May 14, 1990, now U.S. Pat. No. 5,458,878, all of which are incorporated by reference.

Preferred forms of PE contain amino acids 253–364 and 381–608, and are followed by the native sequences REDLK or the mutant sequences KDEL or RDEL. Lysines at positions 590 and 606 may or may not be mutated to glutamine.

In a particularly preferred embodiment, the circularly permuted ligand-PE fusion proteins of this invention comprise the PE molecule designated PE38QQRDEL. This PE molecule is a truncated form of PE composed of amino acids 253–364 and 381– 608. The native C-terminus of PE, REDLK (residues 609–613), is replaced with the sequence RDEL, and Lys-590 and Lys-606 are each mutated to Gln. IL4-PE38QQRDEL contains the toxin fused, through a linker, to the C-terminus of IL4, and IL4(38-37)-PE38QQRDEL contains the toxin fused, through a linker, to the C-terminus of IL4(38-37). The production of IL4(38-37)-PE38QQRDEL is described in detail in Example 2.

The circularly permuted ligand may also be inserted at a point within domain III of the PE molecule. Most preferably the circularly permuted ligand is fused between about amino acid positions 607 and 609 of the PE molecule. This means that the circularly permuted ligand is inserted after about amino acid 607 of the molecule and an appropriate carboxyl end of PE is recreated by placing amino acids about 604–613 of PE after the circularly permuted ligand. Thus, the circularly permuted ligand is inserted within the recombinant PE molecule after about amino acid 607 and is followed by amino acids 604–613 of domain III. The circularly permuted ligand may also be inserted into domain Ib to replace sequences not necessary for toxicity. Debinski, et al. *Mol. Cell. Biol.,* 11: 1751–1753 (1991).

In a preferred embodiment, the PE molecules will be fused to the circularly permuted ligand by recombinant means. The genes encoding protein chains may be cloned in cDNA or in genomic form by any cloning procedure known to those skilled in the art. See for example Sambrook et al., *Molecular Cloning: A Laboratory Manual,* Cold Spring Harbor laboratory, (1989), incorporated by reference herein. Methods of cloning genes encoding PE fused to various ligands are well known to those of skill in the art. See, for example, Siegall et al., *FASEB J.,* 3: 2647–2652 (1989); Chaudhary et al. *Proc. Natl. Acad. Sci. USA,* 84: 4538–4542 (1987), which are incorporated herein by reference.

Those skilled in the art will realize that additional modifications, deletions, insertions and the like may be made to the circularly permuted ligand and PE genes. Especially, deletions or changes may be made in PE or in a linker connecting an antibody gene to PE, in order to increase cytotoxicity of the fusion protein toward target cells or to decrease nonspecific cytotoxicity toward cells without antigen for the antibody. All such constructions may be made by methods of genetic engineering well known to those skilled in the art (see, generally, Sambrook et al., supra) and may produce proteins that have differing properties of affinity, specificity, stability and toxicity that make them particularly suitable for various clinical or biological applications.

Like PE, diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al., *Science,* 175: 901–903 (1972); Uchida et al. *J. Biol. Chem.,* 248: 3838–3844 (1973)).

In a preferred embodiment, the circularly permuted ligand-Diphtheria toxin fusion proteins of this invention have the native receptor-binding domain removed by truncation of the Diphtheria toxin B chain. Particularly preferred is DT388, a DT in which the carboxyl terminal sequence beginning at residue 389 is removed. Chaudhary, et al., *Bioch. Biophys. Res. Comm.,* 180: 545–551 (1991).

Like the PE fusion proteins, the DT molecules will be fused to the circularly permuted ligand by recombinant means. The genes encoding protein chains may be cloned in cDNA or in genomic form by any cloning procedure known to those skilled in the art. Methods of cloning genes encoding DT fused to various ligands are also well known to those of skill in the art. See, for example, Williams et al. *J. Biol. Chem.* 265: 11885–11889 (1990) and copending patent application (U.S. Ser. No. 07/620,939, filed Dec. 3, 1990, pending,) which describe the expression of a number of growth-factor-DT fusion proteins.

The present invention also provides for "dual targeted" immunotoxins in which a circularly permuted ligand is fused to one terminus of the immunotoxin while another targeting ligand (e.g. an antibody, a circularly permuted growth factor, or another circularly permuted ligand) is inserted in the other terminus of the toxin. Thus, for example, a dual targeted PE might comprise a circularly permuted IL4 substituted for domain Ia at the amino terminus of the PE and anti-Tac(Fv) inserted in domain III, between amino acid 604 and 609. Other antibodies may also be suitable. A number of other antibodies have been converted to single-chain immunotoxins, including anti-erbB2, B3, BR96, OVB3, anti-transferrin, Mik-β1 and PR1 (Batra et al., *Mol. Cell. Biol.,* 11: 2200–2205 (1991); Batra et al., *Proc. Nad. Acad. Sci. USA,* 89: 5867–5871 (1992); Brinkmann, et al. *Proc. Natl. Acad. Sci. USA,* 88: 8616–8620 (1991); Brinkmann et al., *Proc. Natl. Acad. Sci. USA,* 90: 547–551 (1993); Chaudhary et al., *Proc. Natl. Acad. Sci. USA,* 87: 1066–1070 (1990); Friedman et al., *Cancer Res.* 53: 334–339 (1993); Kreitman et al., *J. Immunol.,* 149: 2810–2815 (1992); Nicholls et al., *J. Biol. Chem.,* 268: 5302–5308 (1993); and Weis, et al., *Cancer Res.,* 52: 6310–6317 (1992)).

This invention also provides fusion proteins comprising circularly permuted ligands fused to an antibody. The antibody component of the fusion protein may specifically bind antigens characteristic of certain antigen-positive cancer cells (e.g., the $Le^y$ related antigen recognized by monoclonal antibodies B3, BR96, or the erb2 protein recognized by the e23 and other antibodies (Id.) while the circularly permuted ligand specifically binds immune cells bearing the particular receptor for the ligand (e.g. cells bearing IL2 or IL4 receptors). The circularly permuted bifunctional fusion protein thus acts to enhance the interaction between cancer cells and components of the immune systems and binds with higher affinity compared to the bifunctional fusion protein containing the native (unpermuted) ligand.

The antibodies used in the fusion protein include various forms of modified or altered antibodies, such as an intact immunoglobulin, an Fv fragment containing only the light and heavy chain variable regions, an Fv fragment linked by a disulfide bond, an Fab or $(Fab)'_2$ fragment containing the variable regions and parts of the constant regions, a single-chain antibody, a single domain of an antibody, and the like (Bird et al., *Science* 242: 424–426 (1988); Huston et al., *Proc. Nat. Acad. Sci. USA* 85: 5879–5883 (1988); Brinkmann, et al. *Proc. Nat. Acad. Sci. USA*, 90: 7538–7542 (1993). The antibody may be of animal (especially mouse or rat) or human origin or may be chimeric (Morrison et al., *Proc Nat. Acad. Sci. USA* 81: 6851–6855 (1984)) or humanized (Jones et al., *Nature* 321: 522–525 (1986), and published UK patent application #8707252). Methods of producing antibodies suitable for use in the present invention are well known to those skilled in the art and can be found described in such publications as Harlow & Lane, *Antibodies: A Laboratory Manual*, Cold Spring Harbor Laboratory (1988), and Asai, *Methods in Cell Biology* Vol. 37: *Antibodies in Cell Biology*, Academic Press, Inc. New York (1993). region.

An exemplary single chain antibody is B3(Fv), the Fv fragment of antibody B3. This antibody binds a carbohydrate antigen in the $Le^y$ family which is found on the surface of many carcinomas of the colon, stomach, prostate, bladder, ovaries, breast and lung as well as some epidermoid carcinomas. Other antibodies of interest include BR96 (Friedman et al., *Cancer Res.*, 53: 334–339 (1993), e23 to erbB2 (Batra et al, *Proc. Natl. Acad. Sci. USA*, 89: 5867–5871 (1992)), PR1 in prostate cancer (Brinkmann et al., *Proc. Natl. Acad. Sci. USA.*, 90: 547–551 (1993)), and K1 in ovarian cancer (Chang et al. *Int. J. Cancer*, 50: 373–381 (1992).

Means of fusing antibodies to the circularly permuted ligands are well known to those of skill in the art. See, for example, Batra et al., *Mol. Cell. Biol.*, 11: 200–2205 (1991), Chaudhary et al., *Nature*, 339: 394–397 (1989); Chaudhary et al. *Proc. Natl. Acad. Sci. USA*, 87: 1066–1070 (1990); and Brinkmann et al. *Proc. Natl. Acad. Sci. USA*, 88: 8616–8620 (1991) which are incorporated herein by reference.

Other binding proteins besides antibodies may serve a similar function. Thus, this invention includes fusion proteins comprising a circularly permuted ligand fused to one or more binding proteins. These binding proteins may include antibodies, ligands, hormones, growth factors, circularly permuted ligands, circularly permuted hormones, circularly permuted growth factors, and other circularly permuted ligands.

To determine which circularly permuted ligands or fusion proteins containing these factors are preferred, the proteins should be assayed for biological activity. Such assays, well known to those of skill in the art, generally fall into two categories; those that measure the binding affinity of the protein to a particular target, and those that measure the biological activity of the protein.

Binding affinity may be assayed by measuring the ability of the circularly permuted molecule to displace a native (unpermuted) ligand from its target substrate. This may be accomplished by labeling the native ligand and then incubating cells beating the target receptor with a fixed amount of the labeled ligand and various concentrations of circularly permuted ligand. The amount of bound native ligand can be determined by detecting the amount of label bound to the target cell. Unlabeled native ligand can be run as a control. One of skill will recognize that selection of the target cell is determined by the particular ligand. The particular label is chosen to minimally interfere with the binding of the labeled native ligand. Suitable labels are well known to those of skill in the art and include, but are not limited to radioactive labels (e.g., $^{125}I$, $^{32}P$), fluorescent labels (e.g., fluorescein or rhodamine), and enzymatic labels (e.g., horseradish peroxidase). Examples of competitive binding assays may be found in Examples 1(c) and 2(c).

It is possible that the circularly permuted ligand might specifically bind the target receptor and yet fail to show any other biological activity (e.g., internalization within the cell). Therefore, it is often desirable to assay the biological activity of the protein as well as its binding specificity and affinity. Assays for biological activities of various kinds are well known to those of skill in the art. The particular assay depends on the particular activity of the molecule.

For example, where the protein is solely a circularized growth factor, the expected biological activity usually is an increase in growth or proliferation of cells beating the protein's target receptors, but may be growth inhibition or cell differentiation. Conversely, where the circularized growth factor is fused to a cytotoxin, the expected biological activity would be a decrease in cell metabolic rate or possibly cell death. Changes in metabolic rate are easily measured as changes in the rate of uptake of a labelled metabolic substrate in the cells exposed to the test protein as compared to unexposed control cells. Generally, [$^3$H]-thymidine or [$^3$H]-leucine are used as labeled metabolic substrates although other labeled substrates are well known to those of skill in the art. Examples 1(d) and 2(d) detail assays for biological activity for circularly permuted IL4 and the IL4(38-37)-PE38QQRDEL fusion protein respectively.

The recombinant fusion proteins and pharmaceutical compositions of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The recombinant fusion proteins and pharmaceutical compositions of this invention are particularly useful for parenteral administration, such as intravenous administration or administration into a body cavity or lumen of an organ. The compositions for administration will commonly comprise a solution of the circularly permuted ligand fusion protein dissolved in a pharmaceutically acceptable carder, preferably an aqueous carrier. A variety of aqueous carders can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 100 mg per patient per day. Dosages from 0.1 up to about 1000 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the present fusion proteins or a cocktail thereof (i.e., with other proteins) can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

Among various uses of the cytotoxic fusion proteins of the present invention are included a variety of disease conditions caused by specific human cells that may be eliminated by the toxic action of the protein. One preferred application is the treatment of cancer, such as by the use of TGFα or IL4 or IL6 or IGF1 as the circularly permuted ligand or of autoimmune conditions such as graft-versus-host disease, organ transplant rejection, type I diabetes, multiple sclerosis, rheumatoid arthritis, systemic lupus erythematosus, myasthenia gravis and the like caused by T and B cells. The fusion proteins may also be used in vitro, for example, in the elimination of harmful cells from bone marrow before transplant. The circularly permuted ligand portion of the fusion protein is chosen according to the intended use. Proteins on the membranes of T cells that may serve as targets for the circularly permuted ligands include CD2 (T11), CD3, CD4 and CDS. Proteins found predominantly on B cells that might serve as targets include CD10 (CALLA antigen), CD19 and CD20. CD45 is a possible target that occurs broadly on lymphoid cells. These and other possible target lymphocyte target molecules for the circularly permuted ligand proteins are described in *Leucocyte Typing III*, A. J. McMichael, ed., Oxford University Press (19870. Antigens found on cancer cells that may serve as targets for the circularly permuted ligand proteins include carcinoembryonic antigen (CEA), the transferrin receptor, P-glycoprotein, c-erbB2, $Le^{y}$ and antigens described in the Abstracts of the Third International Conference on Monoclonal Antibody Immunoconjugates for Cancer, San Diego, Calif. (1988). Those skilled in the art will realize that circularly permuted ligands may be chosen that bind to receptors expressed on still other types of cells as described above, for example, membrane glycoproteins or ligand or hormone receptors such as epidermal growth factor receptor and the like.

The following examples are offered by way of illustration and are not to be construed as limiting the invention as claimed in any way.

EXAMPLES

The oligonucleotide primers used in the following examples are listed in Table 1 and in Sequence Id. No: 6 through Sequence ID No.: 48, respectively.

TABLE I

Sequence of oligonucleotide primers used in Examples 1 through 6. The sequences are listed in the 5' to 3' direction from left to right.

| Primer | Sequence |
|---|---|
| BK24 | A-ATA-CGA-CTC-ACT-ATA-G |
| BK50 | GGC-ACC-GTT-GCG-AAT-CCG-GCC-GCG |
| BK54 | TGC-TTT-ACG-GGC-TAC-GCC-CAG-GAC-CAG |
| BK55 | GGG-ACC-TCC-GGA-CGA-TTT-GCC-TGA-GGA-GAC-GGT-GAC-CTC-GGT-ACC-TTG-GCC-CCA-GTA |
| BK56 | GGG-ACC-TCC-AGC-TTT-ACT-CTC-GAG-CTT-TGT-CCC-CGA |
| BK63 | CAC-CGT-CCA-GTT-CTG-CGT-GCC |
| BK78 | ATA-CGA-CTC-ACT-ATA-GGG-AGA |
| BK83 | GGG-CAT-AAA-CCC-GGG-CAT-AAA-ACG-CAT-GCA-CCT-ACT-TCA-AGT-TCT-ACA-AAG |
| BK84 | TCA-AGC-TGA-ATT-CTA-GGT-GAG-TGT-TGA-GAT-GAT-GCT-TTG-ACA |
| BK87 | CGG-CCA-CGA-TGC-GTC-CGG-CGT |
| BK96 | GGG-CTT-GGA-TCC-CCC-CCC-ACC-TGA-ACC-TCC-TCC-CCC-GCT-CGA-ACA-CTT-TGA-ATA-TTT |
| BK97 | GAG-GTC-GGA-TCC-GGC-GGA-GGC-GGA-TCT-GGC-GGA-GGT-GGC-TCG-GGC-GGC-AGC-CTG-GCC-GCG |
| BK-110 | TGT-TGC-TCC-GGA-GGT-AAC-GGT-GGG-CAC-AAG-TGC-GAT-ATC-ACC |
| BK-111 | CTT-GTG-CCC-ACC-GTT-ACC-TCC-GGA-CGA-ACA-CTT-TGA-ATA-TTT-CTC |
| BK-112 | CTC-AGT-TGA-AGC-TTT-GGA-GGC-AGC-AAA-GAT-GTC |
| BK-113 | TTT-GCT-GCC-CAT-ATG-AAC-ACA-ACT-GAG-AAG-GAA |
| BK-114 | ACT-CTG-GTA-AGC-TTC-CTT-CAC-AGG-ACA-GGA |

TABLE I-continued

Sequence of oligonucleotide primers used in Examples 1 through 6. The sequences are listed in the 5' to 3' direction from left to right.

| Primer | Sequence |
|---|---|
| BK-115 | CCT-GTG-AAG-CAT-ATG-AAC-CAG-AGT-ACG-TTG-GAA-AAC |
| BK-116 | TAT-TCA-AAG-TAA-GCT-TCC-GGG-GGA-GGA-GGT-TCA |
| BK-117 | GGA-GAT-ATA-CAT-ATG-GAC-ACA-ACT-GAG-AAG-GAA |
| BK-132 | GTT-TAA-CTT-TAA-GCT-TCC-GGA-GGT-CCC-GAG-GAC-ACA-ACT-GAG-AAG-GAA |
| BK-133 | CTC-GGG-ACC-TCG-AGC-TCA-TTT-GGA-GGC-AGC-AAA-GAT |
| BK-135 | ACA-CTC-ACC-GGA-GGT-AAC-GGT-GGG-GCA-CCT-ACT-TCA-AGT-TCT |
| BK-136 | AAA-CTG-AAT-TCA-AGC-TTA-CCT-GGT-GAG-TTT-GGG-ATT |
| BK-137 | AAA-CTC-ACC-CAT-ATG-CTC-ACA-TTT-AAG-TTT |
| BK-138 | AGG-TGC-CCC-ACC-GTT-ACC-TCC-GGT-GAG-TGT-TGA-GAT-GAT |
| BK-139 | GAG-GGC-GGA-GGA-AAC-GGA-GGT-GGG-GCA-CCC-GCC-CGC-TCG-CCC |
| BK-140 | TTC-TAG-AAT-TCA-AGC-TTA-CTC-AGC-AGC-AGT-GTC-TCT |
| BK-141 | ACT-GCT-GCT-CAT-ATG-GAT-GAA-ACA-GTA-GAA-GTC |
| BK-142 | GGG-TGC-CCC-ACC-TCC-GTT-TCC-TCC-GCC-CTC-CTG-GAC-TGG-CTC-CCA |
| BK-143 | GCC-TGC-AGC-CAT-ATG-GCA-CCC-GCC-CGC-TCG-CCC-AGC-CCC |
| BK-144 | CTC-ATG-AAT-TCA-AGC-TTA-CTC-CTG-GAC-TGG-CTC-CCA-GCA-GTC |
| BK-149 | AAT-TCA-AGC-TTC-ACG-TGT-GAG-TTT-GGG-ATT-CTT |
| BK-150 | AAT-TCA-AGA-AGC-TTC-TGC-AGC-AGT-GTC-TCT-ACT |
| BK-151 | CTG-TGC-ACC-CAT-ATG-ACC-GTA-ACA-GAC-ATC |
| BK-152 | GAT-GTC-GTA-AGC-TTT-CAA-CTC-GGT-GCA-CAG |
| BK-153 | ACA-GTG-CAG-CAT-ATG-ACC-CCC-CTG-GGC-CCT-GCC-AGC |
| BK-154 | AAT-CTA-AGC-TTG-GGG-CTG-GGC-AAG-GTG-GCG-TAG |
| BK-155 | GGG-GGC-GGA-GGA-AAC-GGA-GGT-GGG-ACC-CCC-CTG-GGC-CCT-GCC |
| BK-156 | CTG-CAA-AGC-TTG-GCT-GGG-GCA-GCT-GCT |
| BK-157 | TGC-CCC-AGC-CAT-ATG-CTG-CAG-CTG-GCA-GGC-TGC |
| BK-158 | GGT-CCC-ACC-TCC-GTT-TCC-TCC-GCC-GGG-CTG-GGC-AAG-GTG-GCG |
| VK116 | TGG-CGC-GGT-TTC-TAT-ATC-GCC |
| VK281 | GGC-CGG-TCG-CGG-GAA-TTC-TTA-GAG-CTC-GTC-TTT-CGG-CGG-TTT-GCC-GGG |

Example 1

Circularly Permuted IL4: Preparation and Biological Activity a) Construction of mutant plasmids pRKL4038 and pRKL4105

To make the mutant plasmids pRKL4038 and pRKL4105 encoding IL4(38-37) and IL4(105-104) respectively, the DNA sequence encoding recombinant IL4 was circularly permuted by polymerase chain reaction (PCR). The plasmid pGEM-7f (*J. Biol. Chem.* 268: 14065–14070 (1993)), designated herein as pRKL4, encoding native IL4 was used for a template. All amplification primers are listed in Table 1. The primers were made using a synthetic oligonucleotide synthesizer by Bioserv (Gaithersburg, Md., U.S.A.).

PCR was performed using the Gene-Amp kit (Perkin Elmer, USB, Cleveland, Ohio, U.S.A.) according to the protocol supplied with the kit. Plasmids were purified using the Qiagen TIP-500 kit (Qiagen, Chatsworth, Calif., U.S.A.) and Promega magic minipreps (Promega, Madison, Wis., U.S.A.) according to the protocols supplied with the kits.

IL4 codons 1–37 were amplified using primers BK-110 and BK-112. The 5' end of the fragment encoded a GGNGG linker (Seq. Id. No. 50) and the 3' end contained a HindIII site. IL4 codons 38–129 were amplified using BK-113 and BK-111. The 5' end contained an NdeI site and the 3' end encoded the GGNGG linker (Seq. Id. No. 50). Since the 5' end of the first fragment is complementary to the 3' end of the second fragment, the 2 fragments (after partial purification on LMP agarose) could be used as an overlapping template in a 3rd PCR reaction using primers BK-113 and BK-112. The amplified fragment, cut with NdeI and HindIII, encodes IL4 codons 38–129, GGNGG (Seq. Id. No. 50), and IL4 codons 1–37.

IL4 can also be circularly permuted at other residues. IL4 codons 1–104 of pRKL4 were amplified using BK-110 and BK-114, while codons 105–129 were amplified using BK-115 and BK-111. Regions encoding the GGNGG linker (Seq. Id. No. 50) are the same as above. In the 3rd PCR reaction the overlapping template was amplified using BK115 and BK114. The amplified fragment, cut with NdeI and HindIII, produces a fragment encoding IL4 codons 105–129, GGNGG (Seq. Id. No. 50), and IL4 codons 1–104.

The NdeI-HindIII fragments were subcloned into pRKL4 to produce the plasmids pRKL4038 and pRKL4105 encoding IL4(38-37) and IL4(105-104) respectively. These plasmids which encode the circularly permuted growth-factor carry a T7 promoter, a transcription terminator at the end of the open reading frame of the protein, an f1 origin of replication, and a gene for ampicillin resistance.

The entire coding region of each plasmid was sequenced using the Taq Dyedeoxy terminator cycle sequencing kit in conjunction with an automated sequencer (Applied Biosystems, Inc., Foster City, Calif., U.S.A.).

b) Protein expression and purification

To produce the circularly permuted molecules, *E. coli* BL21 (λDE3) cells were transformed (2 ng/100 μl of cells) with plasmid pRKL4038 or plasmid pRKL4105, incubated on ice 30 minutes, incubated at 42° C. for 1 minute, mixed with SOC media (900 μl/100 μl cells), shaken at 37° C. for 1 hour and then spread on L8-AMP plates.

The cells were cultured in superbroth containing ampicillin (100 μg/ml), glucose (5 mg/ml) and extra $MgSO_4$ (1.6 mM). At an $OD_{650nm}$ of about 3, isopropyl-β-D-thiogalactopyranoside (IPTG, USB, Cleveland, Ohio, U.S.A.) was added to a final concentration of 1 mM, and protein expression induced for 90–120 minutes. The harvested cell paste from 1 L of culture was resuspended in 360 ml TES (50 mM Tris-HCl, pH 8.0, 20 mM EDTA, and 0.1M NaCl) and lysozyme (13 ml of 5 mg/ml). After incubating for 30 minutes at 22° C., DNAse (0.8 mg in 0.8 ml $H_2O$) was added and, after shaking and allowing to stand at 22° C. for 30 minutes, the mixture was resuspended and centrifuged. The pellet was resuspended in 360 ml TES+40 ml 25% Triton X-100, incubated at 22° C. for 10 minutes and centrifuged. The pellet was washed two or three more times by resuspension in 360 ml TES+40 ml 25% Triton X-100 and centrifugation, then washed four times by resuspension in 360 ml TES and centrifugation. All resuspensions were performed using a tissuemizer (Thomas Scientific, Swedesboro, N.J., U.S.A.) at 22° C. and centrifugations were performed at 4° C. in a GSA rotor (Sorvall, Wilmington, Del., U.S.A.) at 13,000 RPM for 30–50 minutes.

The purified inclusion body (~120 mg) was resuspended by sonication in 12 ml of 7M guanidine:HCl containing 0.1M Tris, pH 8, 2 mM EDTA, and 65 mM dithioerythritol (DTE) (Sigma, St. Louis, Mo., U.S.A.) and incubated 8–24 hr at 22° C. The denatured-reduced protein was clarified by centrifugation and diluted 100-fold into cold refolding buffer containing 0.1M Tris, pH 8.0, 0.5M L-arginine, 2 mM EDTA, and 0.9 mM oxidized glutathione (GSSG) (Sigma, St. Louis, Mo., U.S.A.).

After incubation at 10° C. for 36–48 hours, the clear solution was dialyzed against 0.02M NaOAc (pH ~4.8) to a conductivity <3.5 mMho. The refolded dialyzed protein was clarified by filtration through a 0.45 μfilter and loaded onto ~10 ml of CM fast flow cation exchange resin (Pharmacia-LKB, Piscataway, N.J., U.S.A.). The column was washed with equilibration buffer (0.02M NaOAc, pH 4.8) and eluted with equilibration buffer containing 0.5M NaCl.

The IL4 routants were further purified by elution from an anion exchange column (Mono-Q, Pharmacia-LKB, Piscataway, N.J., U.S.A.) using a linear NaCl gradient in equilibration buffer. Finally, the protein containing fractions were subjected to size exclusion chromatography using a TSK250 column (60×2.25 cm, Bio-Rad, Hercules, Calif., U.S.A.), equilibrated with 0.1M $NaH_2PO_4$ in 1 mM EDTA. Protein concentration was determined by the Bradford Coomassie plus assay (Pierce Chemical Co., Rockford, Ill., U.S.A.) using bovine serum albumin as a standard. Fractions were selected based on their purity by SDS-PAGE.

Purity of the mutant circularly permuted IL4 molecules was ascertained by SDS-PAGE. Each sample was run on 10–20% tricine gels (Novex, San Diego, Calif.) under reducing and non-reducing conditions. The purified proteins were shown to be greater than 95% pure. Under reducing conditions the gel retention of IL4, IL4(38-37), and IL4(105-104), which are 130, 136, and 135 amino acids in length, respectively was as expected. Under non-reducing conditions the band corresponding to IL4(105-104) migrated at a slightly slower rate than expected.

The amino terminal sequence of each circularly permuted protein, including the initiator methionine, was confirmed by amino acid sequence analysis (M. Lively, Wake Forest University, Winston-Salem, N.C., U.S.A.).

Figure 2A:
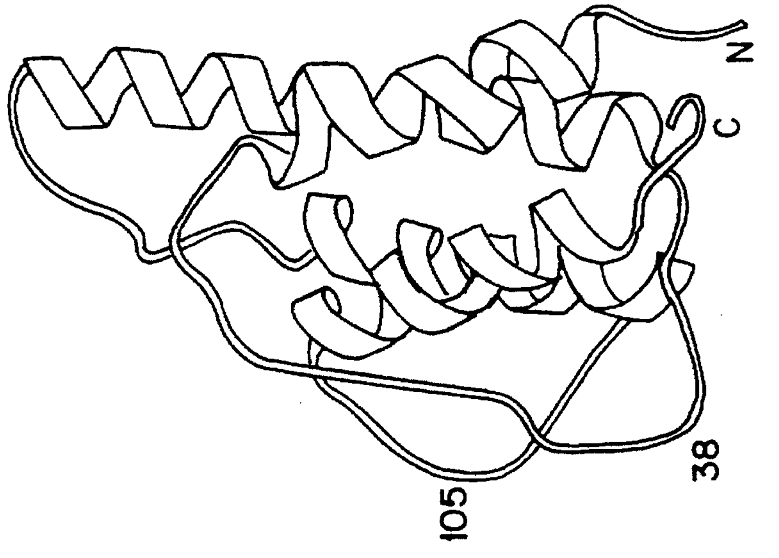
FIG. 2 shows a schematic three dimensional diagram of IL4 and circularly permuted mutants. The three dimensional structure of IL4, based on the NMR coordinates (Powers et al. *Science*, 256: 1673–1677 (1992); Powers et al. *Biochem*, 32: 6744: 6762 (1993)) was converted to the schematic form shown in A by the Molscript Program (Luger et al. *Science*, 243: 206–210 (1989)). The numbering system used here is based on the 129 amino acid mature IL4 protein, of Sequence Id. No.: 2 which, in recombinant form, is preceded by Met (Redfield et al., *Biochemistry*, 30: 11029–11035 (1991). The structures of IL4(38-37) in B and IL4(105-104) in C were based on that of IL4. IL4(38-37) consisted of Met followed by amino acids 38–129, GGNGG (Seq. Id. No. 50), amino acids 1–37 and a C-terminal alaninc. IL4(105-104)

FIG. 2 shows a schematic three dimensional diagram of IL4 and circularly permuted routants IL4(38-38) and IL4 (105-104). The three dimensional structure of IL4, based on the NMR coordinates (Powers et al. *Science,* 256: 1673–1677 (1992); Powers et al. *Biochem,* 32: 6744: 6762 (1993)) kindly provided by M. Clore was converted to the schematic form shown in FIG. 2(A) by the Molscript Program (Luger et al. *Science,* 243: 206–210 (1989), kindly provided by Dr. P. Kraulis. The numbering system used here is based on the 129 amino acid mature IL4 protein, of Sequence ID No.: 3 which, in recombinant form, is preceded by Met (Redfield, et al., *Biochemistry,* 30: 11029–11-35 (1991)).

Figure 2B:
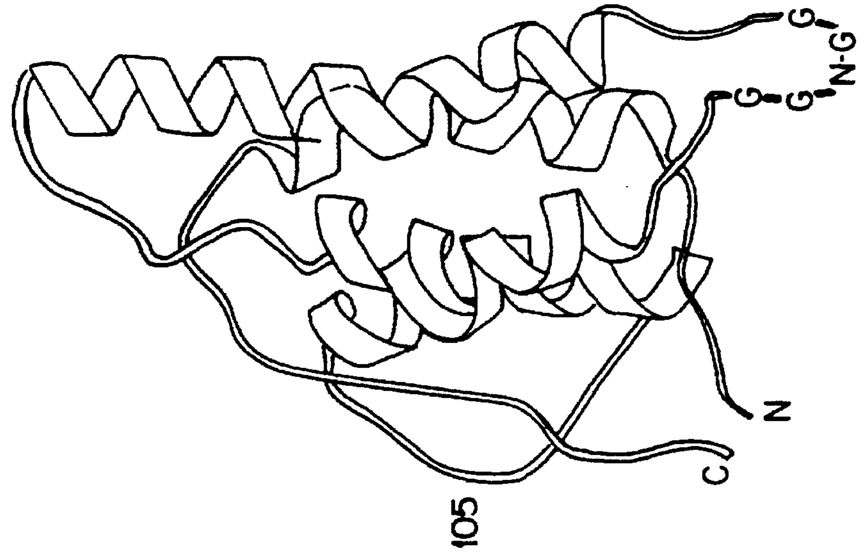
Figure 2C:
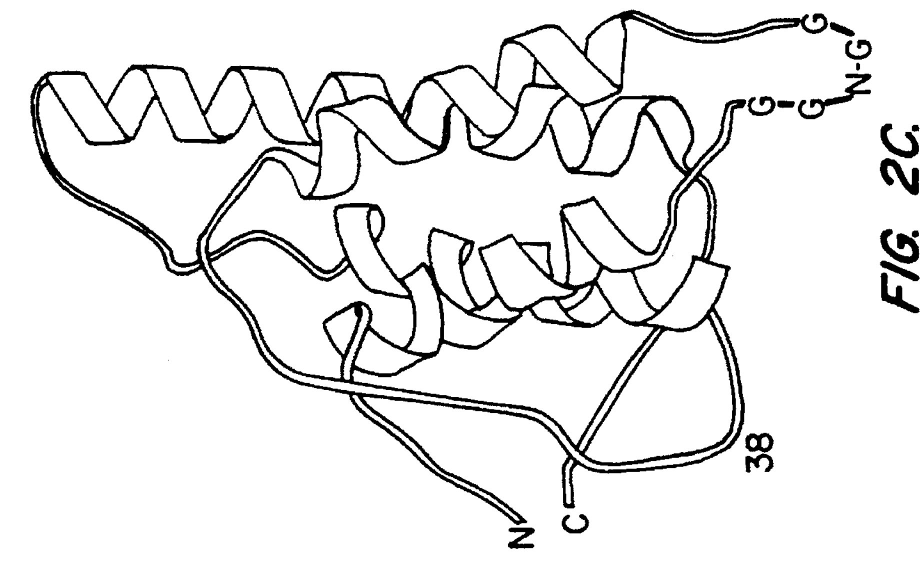

The structures of IL4(38-37) in FIG. 2(B) and IL4(105-104) in FIG. 2(C) were based on that of IL4. IL4(38-37) consisted of Met followed by amino acids 38–129, GGNGG (Seq. Id. No. 50), amino acids 1–37 and a C-terminal alanine. IL4(105-104) consisted of Met followed by amino acids 105-129, GGNGG (Seq. Id. No. 50) and 1–104. For cloning purposes, each IL4 mutant contained alanine at the new C-terminus. This alaninc was residue 104 for IL4(105-104) and constituted an extra residue for IL4(38-37).

c) Binding Affinity of Circularly Permuted IL4

The binding affinity of the circularly permuted IL4 is a measure of the ability of the protein to assume the conformation of native IL4 since it is expected that an incorrectly folded protein will have lost some measure of its binding affinity. To assess their binding affinity, the circularly permuted IL4 molecules were compared to native IL4 in their ability to displace labeled native IL4 ([$^{125}$I]-IL4) from IL4 receptor-bearing cells (FIG. 3(A)).

IL4 was iodinated using the method described by Debinski et al. *J. Biol. Chem.,* 268: 14065–14070 (1993). Then different concentrations of IL4 (O), IL4(38-37) (▲) or IL4(105-104) (□) were incubated with 0.5 nM [$^{125}$I]-IL4 and 2.5×10$^6$ H9 cell in 126λ of media (RPMI containing 10% FBS). After 1–2 hours at 4° C., the cells were centrifuged through phthalate oil and the pellet analyzed in a gamma counter (FIG. 3(A)). The $EC_{50}$, the calculated concentration of protein necessary for 50% displacement of IL4, was 0.19 nM for IL4, 0.22 nM for IL4(38-37), and 0.21 nM for IL4 (105-104). Thus the binding activity of the circularly permuted IL4 routants was similar to that of IL4. Similar results were found in the displacement of [$^{125}$I]-IL4 from the B-cell line DAUDI (data not shown).

To determine if the circularly permuted IL4 mutants would bind well if exposed to IL4 receptor-bearing cells at 4° C., but not at 37° C. the mutants were compared in competition with the cytotoxic activity of the IL4-toxin IL4-PE$^{4E}$ (see Debinski et al. *J. Biol. Chem.,* 268: 14065–14070 (1993)).

On A431 based IL4 receptor-bearing epidermoid cells, 1.2 nM IL4-Pe$^{4E}$ inhibited protein synthesis 98%; 50% of this inhibition was eliminated (binding was out competed) by 1.3 nM, 1.2 nM, and 1.4 nM of IL4, IL4(38-37), IL4(105-104) respectively. Thus, the circularly permuted variants bound well at 4° C. and 37° C. and also compete for IL4 internalization. These data strongly suggest that the secondary and tertiary structures of the circularly permuted IL4 proteins, particularly with regard to cysteine pairing, were very similar to that of IL4. This is in dramatic contrast to murine IL4 which does not bind at all to human IL4 receptors and yet differs only slightly in disulfide bond pairing (Cart et al., *Biochem,* 30: 1515–1523 (1991)).

d) Proliferative Activity of Circularly Permuted IL4

It has previously been shown that mutations in human IL4 which prevent its proliferative activity often affect binding to a greatly diminished extent. Kruse et al., *EMBO J.,* 11: 3237–3244 (1992). It is therefore possible that circularly permuted IL4 routants might bind to the IL4 receptor with full affinity, but be unable to transduce the signal which leads to proliferation. Thus it was desirable to determine the proliferative potential of circularly permuted IL4.

To determine the proliferative activity of the circularly permuted mutants, different concentrations of IL4, IL4(38-37), or IL4(105-105) were incubated with 6×10$^6$ CTLL$^{hIL4R}$ cells in 200 μl of DMEM with 10% FBS for 6 hours and then incubated for 18 hours with [$^3$H]-thymidine (0.5 μCi/well). These murine cells which are transfected with a human IL4 receptor cDNA proliferate in a specific manner when exposed to human IL4. Idzerda et al. *J. Exp. Med.*, 171: 861–873 (1993).

Figure 3B:
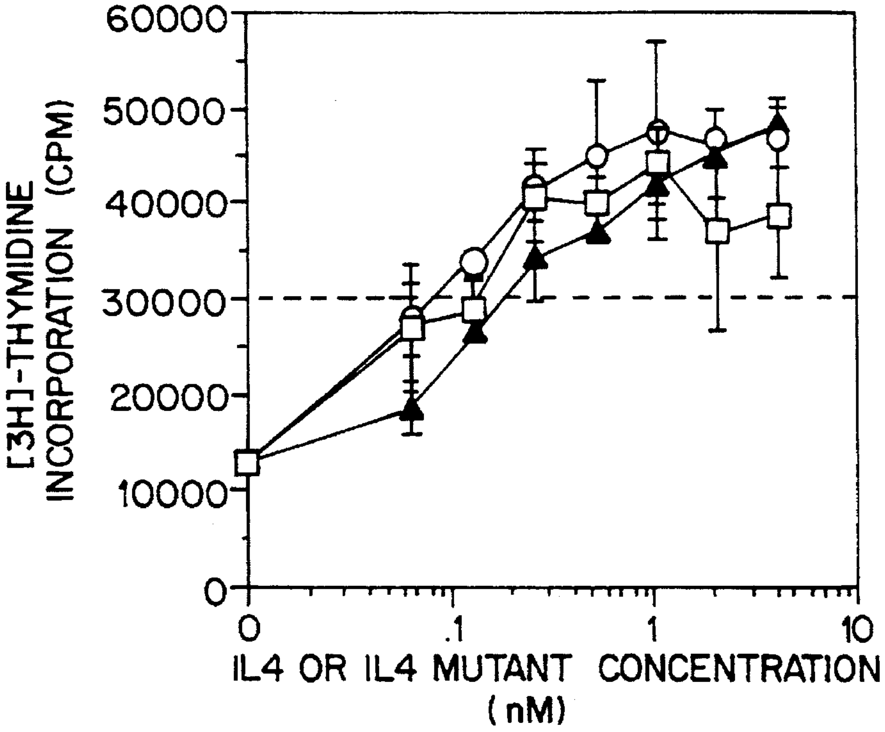

FIG. 3(B) shows [$^3$H]-thymidine incorporation after 24 hours of exposure of the cell to different concentrations of IL4, ILF(38-37), and IL4(105-104). The concentration required for increasing the [$^3$H]-thymidine incorporation to 30,000 counts per minute (cpm), which is approximately half-maximal, was 0.12 nM for IL4, 0.2 nM for IL4(105-104), and 0.24 nM for IL4(38-37). Thus the proliferative activity of the circularly permuted IL4 molecules was 50% to 100% of that of IL4, confirming that the three dimensional structure of the circularly permuted routants was similar to that of IL4.

Example 2

Circularly Permuted IL4-Pseudomonas Exotoxin Fusion Protein: Preparation and Biological Activity.

a) Construction of plasmids pRKL4QRD and pRKL438QRD

DNA sequences encoding IL4(38-37) were prepared as described in Example 1. Plasmids pRKL4QRD and pRKL438QRD, encoding IL4-PE38QQRDSL and IL4(38-37)-PE38QQRDEL, respectively, were constructed by ligating the 0.4 Kb NdeI-HindIII fragment of pRKL4 or pRKL4038, encoding IL4 or IL4(38-37), respectively, to the 4.0 Kb HindIII-NdeI fragment of pRK79QRDE encoding anti-Tac-(Fv)-PE38QQRDEL. PRK79QRDE was constructed by site directed mutagenesis and PCR mutagenesis at the C-terminus of PE. The resulting plasmids, pRKL4QRD and pRKL438QRD, encode IL4-PE38QQRDEL and IL4(38-37)-PE38QQRDEL respectively. IL4-PE38QQRDEL contains the toxin fused to the C-terminus of IL4, and IL4(38-37)-PE38QQRDEL contains the toxin fused to the C-terminus of IL4(38-37). In each case, the 5 amino acids SGGPE (Seq. Id. No. 51) connect the ligand to the toxin.

b) Plasmid expression and purification

Expression and purification of the plasmids pRKL4QRD and pRKL438QRD was performed as in Example 1.

c) Binding Affinity of Circularly Permuted IL4-toxin

Figure 4A:
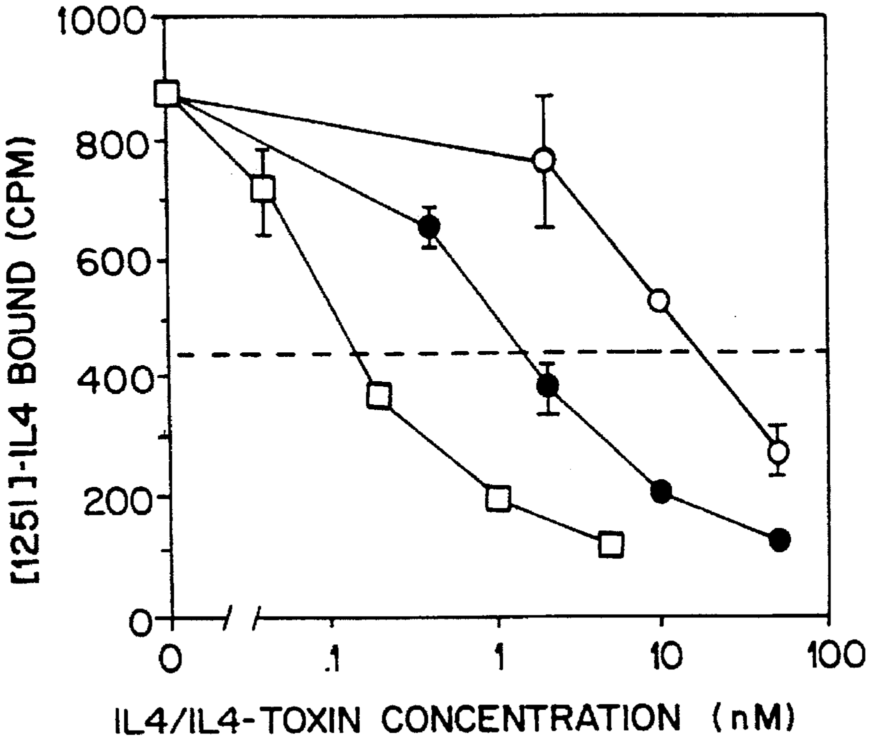

FIG. 4(A) shows the binding activity of circularly permuted IL4-PE fusion protein compared to the native IL4-PE fusion protein. DAUDI cells ($1\times10^6$ cells) in 200 μl aliquots of media (RPMI containing 10% FBS) were incubated at 4° C. for 1–2 hours with [$^{125}$I]-IL4 (0.1 nM) and different concentrations of IL4(□), IL4(38 -37)-PE38QQRDEL (●) or IL4-PE38QQRDEL (○). Each cell aliquot was centrifuged over 150μl of n-butylphthalate and the cell pellet counted in a τ counter. The $EC_{50}$, the concentration of protein needed for 50% displacement of [$^{125}$I]-IL4, was 0.14, 1.4 and 18 for IL4, IL4(38-37)-PE38QQRDEL, and IL4-PE38QQRDEL, respectively. FIG. 4(A) shows that the recombinant fusion toxin IL4(38-37)pPE38QQRDEL was greater than 10 fold more potent than IL4-PE38QQRDEL in displacing [$^{125}$I]-IL4 from IL4 receptor bearing DAUDI cells.

d) Cytotoxicity of Circularly Permuted IL4-toxin

Figure 4B:
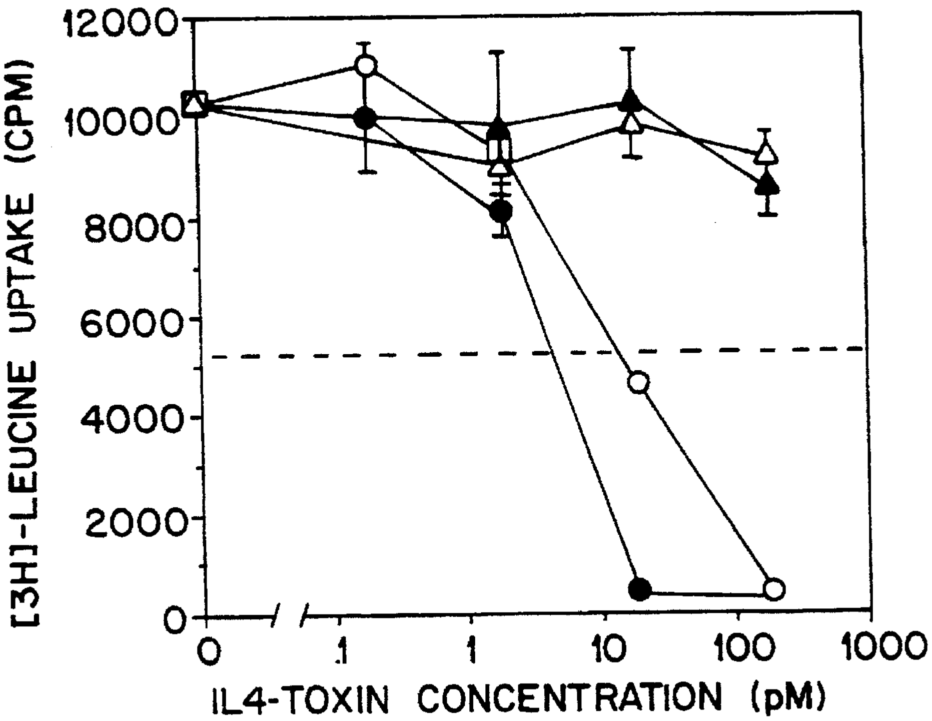

FIG. 4(B) shows the cytotoxic activity of IL4-PE. IL4 receptor-bearing ATAC-4 cells (Kreitman, et al. *Blood*, 83: 426–434 (1994)) were plated at $1–1.5\times10^4$/well for 24 hours, and then incubated in 200 μl aliquots in DMEM containing 5% FBS for 24 hours at 37° C. with different concentrations of IL4(38-37)-PE38QQREL (●) or IL4-PE38QQRDEL (○). Cells were also incubated with IL4(38-37)-PE38QQRDEL (ϵ) or IL4-PE38QQRDEL (Δ) each combined with an excess (10 μg/ml) of IL4. The cells were then pulsed with [$^3$H]-leucine 1 μCi/well for 3–6 hours, harvested and counted. The $IC_{50}$'s, the concentrations needed for 50% inhibition of protein synthesis, were 0.24 and 0.75 ng/ml for IL4(38-37)-PE38QQRDEL and IL4-PE38QQRDEL, respectively.

As shown in FIG. 4(B), the cytotoxic activity was specific for the IL4 receptor and was reversed by an excess of IL4. Toxins fused to circularly permuted forms of IL4 appear to constitute improved reagents for the in vivo treatment of IL4 receptor bearing tumors.

Example 3

Preparation of Circularly Permuted Ligand-Antibody Fusion Proteins.

Plasmid pUL19, encoding B3(Fv)-PE38KDEL (Brinkmann et al., *Proc. Natl. Acad. Sci. USA*, 89:3075–3079 (1992)) is separately amplified with VK116 and BK50, and then BK54 and VK281. The 2 amplified fragments are used as an overlapping template in a 3rd PCR reaction, using VK116 and VK281 as primers. The amplified fragment encodes PE amino acids 466–608 and the C-terminus KDEL. The fragment is cut with EAG1 and EcoRI, and the 0.37 Kb fragment ligated to the 4.5 KB fragment of pULI9. The resulting plasmid, pRKB3F, is identical to pULI9 except codon 493 of PE, ATC, is replaced with ATT which eliminated a BamHI site.

Plasmid pUL120, encoding $B_3(V_H)$-PE38KDEL (Brinkmann et al., *J. Immunol.* 150:2774–2782 (1993)) is amplified with primers BK24 and BK55. The 0.41KB XBAI-HindIII fragment of the amplified DNA is ligated into the 4.0 KB HindIII-XBAI fragment of pRKB3F. The resulting plasmid, pRKB3H2, is identical to pUL120, except that codon 114 of $B_3(V_H)$ (CTG) is replaced with GAG, resulting in a L114E mutation. Codons 112–113 are also changed from GGG-ACT to GGT-ACC, resulting in a new unique KPNI site. Plasmid pRKB3H2 is amplified with the primers BK97 and BK64, and the amplified DNA cut with BAMHI and EcoRI. pRKL4EL, encoding IL4-ELKA (Kreitman et al., *Biochemistry*, submitted), is amplified using primers BK87 and BK96, and the amplified DNA cut with BgLII and BAMHI. The 0.51 KB BgLII-BAMHI fragment and the 1.1 KB BAMHI-EcoRI fragment are then ligated to the 2.9 Kb BgLII-EcoRI fragment of pRK79, which encodes anti-Tac (Fv)-PE38 (Kreitman et al., *Blood* 83:426–434 (1994)). The resulting plasmid, pRKL49K, encodes IL4, followed by the spacer $(GGGGS)_4$ (Seq. Id. No. 55), and PE38KDEL.

Plasmid pRKL4038, encoding IL4 (38-37), is amplified using primers BK117 and BK64, and the DNA cut with NdeI and HindIII.

Plasmid pRKL49K is amplified by primers BK116 and BK63, and the DNA cut with HindIII and SacII. The 0.39 KB NdeI-HindIII fragment and the 0.45 Kb HindIII-SacII fragment are ligated to the 3.6 Kb NdeI-SacII fragment of pRK749K (Spence et al., *Bioconjugate Chem.* 4:63–68 (1993)). The resulting plasmid, pRKDG1K, encodes MD, amino acids 39–129 of IL4, GGNGG (Seq. Id. No. 50), amino acids 1–37 of IL4, the spacer $AS(GGGGS)_4$ (Seq. Id. No. 56), and PE38KDEL. Finally, pRKL4D1K is obtained by ligating the 0.45 KB XBAI-HindIII fragment of pRKL4DG1K to the 4.0 KB XBAI-HindIII fragment of PRK749K. The resulting plasmid pLAD1K differs from pRKL4DG1K in that it encodes the spacer ASGGPE (Seq. Id. No. 57) instead of $AS(GGGGS)_4$ (Seq. Id. No. 56).

Circularly permuted IL4 can be connected to a single-chain Fv, in order to target IL4receptor-bearing immune cells to antigen-positive cancer cells. Plasmid pRKL4D1K, which encodes IL4(38-37)-PE38KDEL, is amplified with primers BK-132 and BK-133. The amplified fragment encoded IL4(38-37) and contained a HindIII site at the 5' end and a SacI site at the 3' end. The 0.4 Kb HindIII-SacI fragment is then ligated to the 3.8 Kb SacI-HindIII fragment of pRKB3F. The resulting plasmid, pRKB3LA38, encodes B3(Fv)-IL4(38-37).

The plasmid is introduced into *E. coli* BL21 (λDE3), expressed by induction with isopropythiogalactoside CIPTG), isolated and purified as described in Example 1.

Example 4

Preparation of Circularly Permuted IL4 Diphtheria Toxin Fusion proteins

To make a diphtheria toxin molecule targeted by circularly permuted ILL4, the 0.4 Kb NdeI-HindIII fragment of pRKL4D1K (see Example 3) is ligated to the 4.2 Kb HindIII-NdeI fragment of pVCDT1-IL2, which encodes DT388-IL2. Chaudhary, et al., *Bioch. Biophys. Res. Comm.*, 180: 545–551 (1991). The resulting plasmid pRKDTL438, encodes DT388-IL4(38-37).

The plasmid is introduced into *E. coli* BL21 (λDE3), expressed by induction with isopropythiogalactoside (IPTG), isolated and purified as described in Example 1.

Example 5

Preparation of Circularly Permuted IL2.

Plasmid pVCDT1-IL2, encoding DT388-IL2 (Chaudhary et al., *Biochem Biophys. Res. Comm.* 180:545–551 (1991)), is amplified with BK-83 and BK-84, and cut with XMAI and EcoRI. The 0.42 Kb XMAI-EcoRI fragment is ligated to the 4.2 Kb XMAI-EcoRI fragment of pVCDT1-IL2. The resulting plasmid, pRKDL2, encodes a protein of sequence identical to that of $DAB_{389}$IL2 (Williams et al., *J. Biol Chem.* 265:11885–11889 (1990)).

To make circularly permuted IL2, pRKDL2, encoding $DAB_{389}$-IL2, is used as a template. IL2 codons 1–38 are amplified using primers BK-135 and BK-136. The 5' end of the amplified fragment encodes the GGNGG linker (Seq. Id. No. 50) and the 3' end contains a HindIII site. IL2 codons 39–127 are amplified using primers BK-137 and BK-138. The 5' end of this fragment contains an NdeI site and the 3' end encodes the GGNGG linker (Seq. Id. No. 50). The overlapping fragments are then amplified in the 3rd PCR reaction using primers BK-137 and BK-136. The 0.4 Kb NdeI-HindIII fragment of this PCR product is ligated to the 3 Kb HindIII-NdeI fragment of pRKL4, which encodes IL4. The resulting plasmid, pRKL2039, encodes IL2(39-38), and contains a stop codon within the HindIII site. Plasmid pRKL2039 is then amplified with the T7 promotor primer BK-78 and BK-149. The 0.4 Kb NdeI-HindIII fragment, which does not contain a stop codon within the HindIII site, is ligated to the 4 Kb HindIII-NdeI fragment of pRKB3F. The resulting plasmid, pRKL2399K, encodes IL2(39-38)-PE38KDEL. The plasmid is introduced into *E. coli* BL21 (λDE3), expressed by induction with isopropythiogalactoside (IPTG), isolated and purified as described in Example 1.

Example 6

Preparation of Circularly Permuted GM-CSF and G-CSF.

To make circularly permuted GM-CSF or G-CSF, templates encoding the native forms of these molecules are first cloned from a spleen eDNA library using either primers BK-143 and BK-144 or BK-153 and BK-154, respectively. GM-CSF codons 1–35 are amplified using BK-139 and BK-140, while GM-CSF codons 36–127 are amplified using primers BK-141 and BK-142. The 5' end of the first fragment and the 3' end of the second fragment both encode for a GGGNGGG linker (Seq. Id. No. 52). The overlapping products are amplified in the 3rd PCR reaction using primers BK-141 and BK-140. The 0.4 Kb NdeI-HindIII fragment, which contains a stop codon within the HindIII site, is then ligated to the 3 KB HindIII-NdeI fragment of PRKL4, resulting in pRKGM036, which encodes GM-CSF(36-35). Plasmid pRKGM036 is then amplified with primers BK-78 and BK-150, and the 0.4 Kb NdeI-HindIII fragment, which does not contain a stop codon within the HindIII site, is ligated to the 4 Kb HindIII-NdeI fragment of pRKB3F. The resulting plasmid, pRKGM369K, encodes GM-CSF(36-35) -PE38KDEL.

G-CSF codons 1–68 are amplified using primers BK-155 and BK-156, and codons 69–173 amplified using primers BK-157 and BK-158. The 5' end of the first fragment and the 3' end of the second fragment both encode the GGGNGGG linker (Seq. Id. No. 52). The overlapping products are amplified in the third PCR reaction using primers BK-157 and BK-156, and the 0.5 Kb NdeI-HindIII fragment ligated to the 4 Kb HindIII-NdeI fragment of pRKB3F. The resulting plasmid, pRKG699K, encodes G-CSF(69-68)-PE38KDEL.

The plasmid is introduced into *E. coli* BL21 (λDE3), expressed by induction with isopropythiogalactoside (IPTG), isolated and purified as described in Example 1.

What is claimed is:

1. A fusion protein comprising a modified interleukin 4 (IL4) that is a modification of an original IL4 having amino acid residues numbered sequentially 1 through J with an amino terminus at residue 1 and a carboxyl terminus at residue J, said fusion protein having the following formula:

$$(T^1)_a—(S^1)_b—X^1—(L)_c—X^2—(S^2)_d—(T^2)_e$$

in which:

$X^1$ is a peptide consisting of an amino acid sequence having the sequence of residues n+1 through J of said original IL4;

L is a linker;

$X^2$ is a peptide consisting of an amino acid sequence having the sequence of residues 1 through n of said original IL4;

$S^1$ and $S^2$ are peptide spacers;

n is an integer ranging from 1 to J−1;

b, c, and d are each independently 0 or 1;

a and e are each either 0 or 1, provided that a and e cannot both be 0; and $T^1$ and $T^2$ are cytotoxins.

2. The fusion protein of claim 1, wherein said cytotoxin is a Pseudomonas exotoxin in which domain Ia is lacking or a Diphtheria toxin in which the native receptor-binding domain is removed by truncation of the Diphtheria toxin B chain.

3. The fusion protein of claim 2, in which:

a is zero;

b is zero;

c is 1;

d is 1;

e is 1; and $T^2$ is a Pseudomonas exotoxin in which domain Ia is lacking.

4. The fusion protein of claim 3, in which:

$X^1$ consists of methionine followed by the amino acid sequence having the sequence of residues 38 through 129 of SEQ ID NO: 3 (IL4);

L is GGNGG (SEQ ID NO: 50);

$X^2$ consists of the amino acid sequence having the sequence of residues 1 through 37 of SEQ ID NO: 3 (IL4);

$S^2$ is SGGPE (SEQ ID NO: 51); and $T^2$ is PE38QQRDEL.

5. The fusion protein of claim 3, in which:

$X^1$ consists of methionine followed by the amino acid sequence having the sequence of residues 105 through 129 of SEQ ID NO: 3 (IL4);

L is GGNGG (SEQ ID NO: 50);

$X^2$ consists of the amino acid sequence having the sequence of residues 1 through 104 of SEQ ID NO: 3 (IL4);

$S^2$ is SGGPE (SEQ ID NO: 51); and $T^2$ is PE38QQRDEL.

6. The fusion protein of claim 2, in which:

a is 1;

b is 1;

c is 1;

d is zero;

e is zero; and $T^1$ is a truncated Diphtheria toxin.

7. The fusion protein of claim 6, in which:

$X^1$ consists of methionine followed by the amino acid sequence having the sequence of residues 38 through 129 of SEQ ID NO: 3 (IL4);

L is GGNGG (SEQ ID NO: 50);

$X^2$ consists of the amino acid sequence having the sequence of residues 1 through 37 of SEQ ID NO: 3 (IL4);

$S^1$ is HM; and $T^1$ is DT388.

8. The fusion protein of claim 6, in which:

$X^1$ consists of methionine followed by the amino acid sequence having the sequence of residues 105 through 129 of SEQ ID NO: 3 (IL4);

L is GGNGG (SEQ ID NO: 50);

$X^2$ consists of the amino acid sequence having the sequence of residues 1 through 104 of SEQ ID NO: 3 (IL4);

$S^1$ is RPHMAD (SEQ ID NO: 53); and $T^1$ is DT388.

9. A fusion protein comprising a modified interleukin 2 (IL2) that is a modification of an original IL2 having amino acid residues numbered sequentially 1 through J with an amino terminus at residue 1 and a carboxyl terminus at residue J, said fusion protein having the following formula:

$$(T^1)_a-(S^1)_b-X^1-(L)_c-X^2-(S^2)_d-(T^2)_e$$

in which:

$X^1$ is a peptide consisting of an amino acid sequence having the sequence of residues n+1 through J of said original IL2;

L is a linker;

$X^2$ is a peptide consisting of an amino acid sequence having the sequence of residues 1 through n of said original IL2;

$S^1$ and $S^2$ are peptide spacers;

n is an integer ranging from 1 to J–1;

b, c, and d are each independently 0 or 1;

a and e are each either 0 or 1, provided that a and e cannot both be 0; and $T^1$ and $T^2$ are cytotoxins.

10. The fusion protein of claim 9, wherein said cytotoxin is a Pseudomonas exotoxin in which domain Ia is lacking or a Diphtheria toxin in which the native receptor-binding domain is removed by truncation of the Diphtheria toxin B chain.

11. The fusion protein of claim 10, in which:

$X^1$ consists of methionine followed by the amino acid sequence having the sequence of residues 39 through 134 of SEQ ID NO: 4 (IL2);

L is GGNGG (SEQ ID NO: 50);

$X^2$ consists of the amino acid sequence having the sequence of residues 1 through 38 of SEQ ID NO: 4 (IL2);

$S^2$ is SGGPE (SEQ ID NO: 51); and $T^2$ is PE38QQRDEL.

12. A fusion protein comprising a modified granulocyte macrophage colony stimulating factor (GM-CSF) that is a modification of an original GM-CSF having amino acid residues numbered sequentially 1 through J with an amino terminus at residue 1 and a carboxyl terminus at residue J, said fusion protein having the following formula:

$$(T^1)_a-(S^1)_b-X^1-(L)_c-X^2-(S^2)_d-(T^2)_e$$

in which:

$X^1$ is a peptide consisting of an amino acid sequence having the sequence of residues n+1 through J of said original GM-CSF;

L is a linker;

$X^2$ is a peptide consisting of an amino acid sequence having the sequence of residues 1 through n of said original GM-CSF;

$S^1$ and $S^2$ are peptide spacers;

n is an integer ranging from 1 to J–1;

b, c, and d are each independently 0 or 1;

a and e are each either 0 or 1, provided that a and e cannot both be 0; and $T^1$ and $T^2$ are cytotoxins.

13. The fusion protein of claim 12, wherein said cytotoxin is a Pseudomonas exotoxin in which domain Ia is lacking or a Diphtheria toxin in which the native receptor-binding domain is removed by truncation of the Diphtheria toxin B chain.

14. The fusion protein of claim 12, in which:

$X^1$ consists of methionine followed by the amino acid sequence having the sequence of residues 36 through 128 of SEQ ID NO: 5 (GM-CSF);

L is GGGNGGG (SEQ ID NO: 52);

$X^2$ consists of the amino acid sequence having the sequence of residues 1 through 35 of SEQ ID NO: 5 (GM-CSF);

$S^2$ is SGGPE (SEQ ID NO: 51); and $T^2$ is PE38QQRDEL.

15. A fusion protein comprising a modified granulocyte colony stimulating factor (G-CSF) that is a modification of an original G-CSF having amino acid residues numbered sequentially 1 through J with an amino terminus at residue 1 and a carboxyl terminus at residue J, said fusion protein having the following formula:

$$(T^1)_a\text{—}(S^1)_b\text{—}X^1\text{—}(L)_c\text{—}X^2\text{—}(S^2)_d\text{—}(T^2)_e$$

in which:

$X^1$ is a peptide consisting of an amino acid sequence having the sequence of residues n+1 through J of said original G-CSF;

L is a linker;

$X^2$ is a peptide consisting of an amino acid sequence having the sequence of residues 1 through n of said original G-CSF;

$S^1$ and $S^2$ are peptide spacers;

n is an integer ranging from 1 to J−1;

b, c, and d are each independently 0 or 1;

a and e are each either 0 or 1, provided that a and e cannot both be 0; and $T^1$ and $T^2$ are cytotoxins.

16. The fusion protein of claim 15, wherein said cytotoxin is a Pseudomonas exotoxin in which domain Ia is lacking or a Diphtheria toxin in which the native receptor-binding domain is removed by truncation of the Diphtheria toxin B chain.

17. The fusion protein of claim 16 , in which:

$X^1$ consists of methionine followed by the amino acid sequence having the sequence of residues 69 through 175 of SEQ ID NO: 6 (G-CSF);

L is GGGNGGG (SEQ ID NO: 52);

$X^2$ consists of the amino acid sequence having the sequence of residues 1 through 68 of SEQ ID NO: 6 (G-CSF);

$S^2$ is SGGPE (SEQ ID NO: 51); and $T^2$ is PE38QQRDEL.

* * * * *